(12) United States Patent
Behzadi et al.

(10) Patent No.: US 11,969,336 B2
(45) Date of Patent: Apr. 30, 2024

(54) CONNECTIVE TISSUE GRAFTING

(71) Applicant: Kambiz Behzadi, Pleasanton, CA (US)

(72) Inventors: Kambiz Behzadi, Pleasanton, CA (US); Michael E. Woods, Brisbane, CA (US)

(73) Assignee: Kambiz Behzadi, Pleasanton, CA (US)

( * ) Notice: Subject to any disclaimer, the term of this patent is extended or adjusted under 35 U.S.C. 154(b) by 103 days.

(21) Appl. No.: 16/596,410

(22) Filed: Oct. 8, 2019

(65) Prior Publication Data
US 2020/0397561 A1    Dec. 24, 2020

Related U.S. Application Data

(63) Continuation-in-part of application No. 16/595,341, filed on Oct. 7, 2019.

(60) Provisional application No. 62/743,042, filed on Oct. 9, 2018, provisional application No. 62/742,851, filed on Oct. 8, 2018.

(51) Int. Cl.
    *A61F 2/08*      (2006.01)

(52) U.S. Cl.
    CPC ..... *A61F 2/0811* (2013.01); *A61F 2002/0841* (2013.01); *A61F 2002/0882* (2013.01); *A61F 2240/008* (2013.01)

(58) Field of Classification Search
    CPC ................................ A61B 17/86; A61B 17/16
    See application file for complete search history.

(56) References Cited

U.S. PATENT DOCUMENTS

| | | | |
|---|---|---|---|
| 1,455,621 A | 5/1923 | Joyner | |
| 2,121,193 A | 6/1938 | Erich | |
| 3,412,733 A | 11/1968 | Ross | |
| 3,818,514 A | 6/1974 | Clark | |
| 3,874,003 A | 4/1975 | Moser et al. | |
| 4,135,517 A | 1/1979 | Reale | |
| 4,301,551 A | 11/1981 | Dore et al. | |
| 4,341,206 A | 7/1982 | Perrett et al. | |
| 4,457,306 A | 7/1984 | Borzone | |

(Continued)

FOREIGN PATENT DOCUMENTS

| | | |
|---|---|---|
| EP | 1433445 A1 | 6/2004 |
| WO | 2007096476 A2 | 8/2007 |

(Continued)

OTHER PUBLICATIONS

PCT International Search Report for International application No. PCT/US17/26417, dated Jul. 3, 2017.

(Continued)

*Primary Examiner* — Yashita Sharma

(74) *Attorney, Agent, or Firm* — Patent Law Offices Michael E. Woods; Michael E. Woods

(57) ABSTRACT

A system and method for an improved connective tissue repair option that reduces disadvantages of conventional fixation options. Biologic press fit fixation of a connective tissue unit may include in situ expansion of a pre-compressed connective tissue unit within a prepared bone tunnel of a portion of bone. An external opening accessing a cavity of the prepared bone tunnel may be smaller than that of the cavity such that expansion of the installed/compressed connective tissue unit increases lateral fixation forces exerted by the expanding/decompressing compressed connective tissue unit within the bone tunnel.

3 Claims, 16 Drawing Sheets

(56) References Cited

U.S. PATENT DOCUMENTS

| | | | |
|---|---|---|---|
| 4,530,114 A | 7/1985 | Tepic | |
| 4,608,019 A | 8/1986 | Kumabe et al. | |
| 4,608,053 A | 8/1986 | Keller | |
| 4,712,951 A | 12/1987 | Brown | |
| 4,728,329 A * | 3/1988 | Mansat | A61F 2/08 623/13.19 |
| 5,108,400 A | 4/1992 | Appel et al. | |
| 5,133,765 A | 7/1992 | Cuilleron | |
| 5,318,570 A | 6/1994 | Hood et al. | |
| 5,358,532 A | 10/1994 | Evans et al. | |
| 5,431,657 A | 7/1995 | Rohr | |
| 5,534,006 A | 7/1996 | Szabo et al. | |
| 5,591,164 A | 1/1997 | Nazre et al. | |
| 5,665,091 A | 9/1997 | Noble et al. | |
| 5,693,088 A * | 12/1997 | Lazarus | A61F 2/07 623/1.35 |
| 5,702,473 A | 12/1997 | Albrektsson et al. | |
| 5,713,901 A | 2/1998 | Tock | |
| 5,769,092 A | 6/1998 | Williamson, Jr. | |
| 5,806,518 A | 9/1998 | Mittelstadt | |
| 5,849,015 A | 12/1998 | Haywood et al. | |
| 5,980,528 A | 11/1999 | Salys | |
| 6,048,365 A | 4/2000 | Burrows et al. | |
| 6,110,179 A | 8/2000 | Flivik et al. | |
| 6,146,425 A | 11/2000 | Hoermansdoerfer | |
| 6,161,545 A | 12/2000 | Chow | |
| 6,197,062 B1 | 3/2001 | Fenlin | |
| 6,204,592 B1 | 3/2001 | Hur | |
| 6,231,612 B1 | 5/2001 | Balay et al. | |
| 6,585,771 B1 | 7/2003 | Buttermilch et al. | |
| 6,659,997 B1 | 12/2003 | Casutt | |
| 7,036,211 B1 | 5/2006 | Panks | |
| 7,645,281 B2 | 1/2010 | Marik | |
| 7,875,083 B2 | 1/2011 | Sudmann | |
| 8,167,823 B2 | 5/2012 | Nycz et al. | |
| 8,328,849 B2 | 12/2012 | Nydegger et al. | |
| 8,603,100 B2 | 12/2013 | Muller | |
| 8,876,529 B2 | 11/2014 | Mayer et al. | |
| 9,211,362 B2 * | 12/2015 | Hwang | A61L 27/3641 |
| 9,232,968 B2 | 1/2016 | Moumene et al. | |
| 9,999,518 B2 | 6/2018 | Mani et al. | |
| 10,251,663 B2 | 4/2019 | Behzadi | |
| 10,299,930 B2 | 5/2019 | Behzadi | |
| 10,849,766 B2 | 12/2020 | Behzadi | |
| 10,864,083 B2 | 12/2020 | Behzadi | |
| 10,905,456 B2 | 2/2021 | Behzadi | |
| 10,912,655 B2 | 2/2021 | Behzadi et al. | |
| 11,026,809 B2 | 6/2021 | Behzadi et al. | |
| 2002/0082695 A1 | 6/2002 | Neumann | |
| 2002/0183851 A1 | 12/2002 | Spiegelberg et al. | |
| 2003/0065398 A1 | 4/2003 | Cueille et al. | |
| 2003/0229357 A1 | 12/2003 | Dye | |
| 2004/0019382 A1 * | 1/2004 | Amirouche | A61B 5/4533 623/18.11 |
| 2004/0044397 A1 | 3/2004 | Stinson | |
| 2004/0097952 A1 | 5/2004 | Sarin et al. | |
| 2005/0004680 A1 | 1/2005 | Saladino et al. | |
| 2005/0015154 A1 | 1/2005 | Lindsey et al. | |
| 2005/0101962 A1 | 5/2005 | Schwenke et al. | |
| 2005/0154398 A1 | 7/2005 | Miniaci et al. | |
| 2005/0209597 A1 | 9/2005 | Long et al. | |
| 2006/0015110 A1 | 1/2006 | Pepper | |
| 2006/0142754 A1 | 6/2006 | Irion et al. | |
| 2006/0189989 A1 | 8/2006 | Bert | |
| 2006/0247638 A1 | 11/2006 | Trieu et al. | |
| 2007/0005144 A1 | 1/2007 | Leisinger et al. | |
| 2007/0162038 A1 | 7/2007 | Tuke | |
| 2007/0219641 A1 | 9/2007 | Dorr et al. | |
| 2007/0233131 A1 | 10/2007 | Song et al. | |
| 2008/0091271 A1 | 4/2008 | Bonitati et al. | |
| 2008/0109085 A1 | 5/2008 | Tulkis et al. | |
| 2008/0234833 A1 | 9/2008 | Bandoh et al. | |
| 2008/0255560 A1 | 10/2008 | Myers et al. | |
| 2009/0112265 A1 | 4/2009 | Hudgins et al. | |
| 2009/0192626 A1 | 7/2009 | Keefer et al. | |
| 2009/0248083 A1 | 10/2009 | Patterson et al. | |
| 2009/0292321 A1 * | 11/2009 | Collette | A61F 2/0811 606/303 |
| 2010/0023014 A1 | 1/2010 | Romagnoli et al. | |
| 2010/0249796 A1 | 9/2010 | Nycz | |
| 2011/0004318 A1 | 1/2011 | Tulkis et al. | |
| 2011/0178521 A1 | 7/2011 | Siravo et al. | |
| 2011/0264009 A1 | 10/2011 | Walter et al. | |
| 2012/0172939 A1 | 7/2012 | Pedicini | |
| 2012/0209277 A1 | 8/2012 | Leparmentier et al. | |
| 2012/0215257 A1 * | 8/2012 | McDevitt | A61F 2/08 606/228 |
| 2012/0330429 A1 | 12/2012 | Axelson, Jr. et al. | |
| 2013/0204264 A1 | 8/2013 | Mani et al. | |
| 2013/0211535 A1 | 8/2013 | Cueille | |
| 2013/0218160 A1 | 8/2013 | Bjorn et al. | |
| 2013/0226189 A1 | 8/2013 | Young | |
| 2013/0261762 A1 | 10/2013 | Kennedy | |
| 2014/0012391 A1 | 1/2014 | Gugler et al. | |
| 2014/0058526 A1 | 2/2014 | Meridew et al. | |
| 2014/0128986 A1 | 5/2014 | Podolsky | |
| 2014/0135773 A1 | 5/2014 | Stein et al. | |
| 2014/0135791 A1 | 5/2014 | Nikou et al. | |
| 2014/0207123 A1 | 7/2014 | Mueller | |
| 2014/0257293 A1 | 9/2014 | Axelson, Jr. et al. | |
| 2014/0275940 A1 | 9/2014 | Hladio et al. | |
| 2014/0303743 A1 | 10/2014 | Choudhury et al. | |
| 2014/0330281 A1 | 11/2014 | Aghazadeh | |
| 2014/0363481 A1 | 12/2014 | Pasini et al. | |
| 2014/0370462 A1 | 12/2014 | Porter et al. | |
| 2014/0371897 A1 | 12/2014 | Lin et al. | |
| 2015/0005777 A1 | 1/2015 | Ferro et al. | |
| 2015/0182350 A1 | 7/2015 | Behzadi | |
| 2015/0182351 A1 | 7/2015 | Behzadi | |
| 2015/0196343 A1 | 7/2015 | Donald et al. | |
| 2015/0201918 A1 | 7/2015 | Kumar et al. | |
| 2015/0216668 A1 | 8/2015 | Smith | |
| 2015/0282856 A1 | 10/2015 | Haiat et al. | |
| 2016/0029952 A1 | 2/2016 | Hunter | |
| 2016/0058519 A1 | 3/2016 | Herr | |
| 2016/0166390 A1 | 6/2016 | Dye et al. | |
| 2016/0206430 A1 | 7/2016 | Grostefon et al. | |
| 2016/0206433 A1 | 7/2016 | Grostefon et al. | |
| 2016/0220315 A1 | 8/2016 | Falardeau et al. | |
| 2016/0338751 A1 | 11/2016 | Kellar et al. | |
| 2017/0056205 A1 | 3/2017 | Biegun et al. | |
| 2017/0095313 A1 | 4/2017 | van der Weide et al. | |
| 2017/0196506 A1 | 7/2017 | Behzadi | |
| 2017/0196701 A1 | 7/2017 | Behzadi et al. | |
| 2017/0196704 A1 | 7/2017 | Behzadi et al. | |
| 2017/0196705 A1 | 7/2017 | Behzadi | |
| 2017/0196706 A1 | 7/2017 | Behzadi | |
| 2017/0196707 A1 | 7/2017 | Behzadi | |
| 2017/0196708 A1 | 7/2017 | Behzadi et al. | |
| 2017/0196710 A1 | 7/2017 | Behzadi | |
| 2017/0196711 A1 | 7/2017 | Behzadi | |
| 2017/0290666 A1 | 10/2017 | Behzadi | |
| 2017/0290667 A1 | 10/2017 | Behzadi | |
| 2017/0325972 A1 | 11/2017 | Steif | |
| 2017/0340448 A1 | 11/2017 | Behzadi | |
| 2017/0340456 A1 | 11/2017 | Behzadi | |
| 2017/0354505 A1 | 12/2017 | Behzadi | |
| 2018/0049891 A1 | 2/2018 | Termanini | |
| 2018/0116740 A1 * | 5/2018 | Gogarty | A61B 34/10 |
| 2018/0235764 A1 | 8/2018 | Moore et al. | |
| 2018/0235765 A1 | 8/2018 | Welker et al. | |
| 2018/0296364 A1 | 10/2018 | Harris et al. | |
| 2018/0325695 A1 | 11/2018 | Wozencroft | |
| 2019/0336307 A1 | 11/2019 | Sungu et al. | |
| 2020/0069279 A1 | 3/2020 | Behzadi et al. | |
| 2020/0069280 A1 | 3/2020 | Behzadi et al. | |
| 2020/0205988 A1 | 7/2020 | Behzadi et al. | |
| 2020/0261232 A1 | 8/2020 | Mistry | |

(56) References Cited

U.S. PATENT DOCUMENTS

2020/0297499 A1    9/2020    Behzadi et al.
2022/0249236 A1    8/2022    Matyas et al.

FOREIGN PATENT DOCUMENTS

WO      2017029173 A1    2/2017
WO      2018031752 A1    2/2018

OTHER PUBLICATIONS

PCT Written Opinion of The International Searching Authority for International application No. PCT/US17/26417 dated Jul. 3, 2017.
International Search Report regarding International application No. PCT/US2017/037042 dated Oct. 6, 2017.
Written Opinion of the International Searching Authority regarding International application No. PCT/US2017/037042 dated Oct. 6, 2017.
International Search Report for International application No. PCT/US2017/012753, dated May 5, 2017.
Written Opinion of the International Searching Authority for International application No. PCT/US2017/012753 dated May 5, 2017.
International Search Report for International application No. PCT/US2017/046261, dated Oct. 18, 2017.
Written Opinion of the International Searching Authority for International application No. PCT/US2017/046261, dated Oct. 18, 2017.
U.S. Appl. No. 17/807,232, filed Jun. 16, 2022, Kambiz Behzadi et al.
U.S. Appl. No. 17/807,268, filed Jun. 16, 2022, Kambiz Behzadi et al.
U.S. Appl. No. 17/807,328, filed Jun. 16, 2022, Kambiz Behzadi.
U.S. Appl. No. 17/814,807, filed Jul. 25, 2022, Kambiz Behzadi et al.
U.S. Appl. No. 17/821,159, filed Aug. 19, 2022, Kambiz Behzadi.
U.S. Appl. No. 17/823,955, filed Aug. 31, 2022, Kambiz Behzadi.
U.S. Appl. No. 62/277,294, filed Jan. 11, 2016, Kambiz Behzadi.
U.S. Appl. No. 62/353,024, filed Jun. 21, 2016, Kambiz Behzadi.
U.S. Appl. No. 62/355,657, filed Jun. 28, 2016, Kambiz Behzadi.
U.S. Appl. No. 62/373,515, filed Aug. 11, 2016, Kambiz Behzadi.
U.S. Appl. No. 62/651,077, filed Mar. 31, 2018, Kambiz Behzadi.
U.S. Appl. No. 62/742,851, filed Oct. 8, 2018, Kambiz Behzadi.
U.S. Appl. No. 62/743,042, filed Oct. 9, 2018, Kambiz Behzadi et al.
U.S. Appl. No. 15/202,434, filed Jul. 5, 2016, Kambiz Behzadi.
U.S. Appl. No. 15/234,782, filed Aug. 11, 2016, Kambiz Behzadi et al.
U.S. Appl. No. 15/234,880, filed Aug. 11, 2016, Kambiz Behzadi et al.
U.S. Appl. No. 15/235,032, filed Aug. 11, 2016, Kambiz Behzadi et al.
U.S. Appl. No. 15/235,053, filed Aug. 11, 2016, Kambiz Behzadi.
U.S. Appl. No. 15/284,091, filed Oct. 3, 2016, Kambiz Behzadi.
U.S. Appl. No. 15/362,675, filed Nov. 28, 2016, Kambiz Behzadi.
U.S. Appl. No. 15/396,785, filed Jan. 2, 2017, Kambiz Behzadi et al.
U.S. Appl. No. 15/398,996, filed Jan. 5, 2017, Kambiz Behzadi.
U.S. Appl. No. 15/453,219, filed Mar. 8, 2017, Kambiz Behzadi.
U.S. Appl. No. 15/592,229, filed May 11, 2017, Kambiz Behzadi.
U.S. Appl. No. 15/687,324, filed Aug. 25, 2017, Kambiz Behzadi.
U.S. Appl. No. 15/716,529, filed Sep. 27, 2017, Kambiz Behzadi et al.
U.S. Appl. No. 15/716,533, filed Sep. 27, 2017, Kambiz Behzadi.
U.S. Appl. No. 16/030,603, filed Jul. 9, 2018, Kambiz Behzadi.
U.S. Appl. No. 16/030,824, filed Jul. 9, 2018, Kambiz Behzadi.
U.S. Appl. No. 16/154,033, filed Oct. 8, 2018, Kambiz Behzadi et al.
U.S. Appl. No. 16/276,639, filed Feb. 15, 2019, Kambiz Behzadi.
U.S. Appl. No. 16/278,085, filed Feb. 16, 2019, Kambiz Behzadi.
U.S. Appl. No. 16/278,668, filed Feb. 18, 2019, Kambiz Behzadi.
U.S. Appl. No. 16/374,750, filed Apr. 4, 2019, Kambiz Behzadi et al.
U.S. Appl. No. 16/375,736, filed Apr. 4, 2019, Kambiz Behzadi et al.
U.S. Appl. No. 16/571,180, filed Sep. 15, 2019, Kambiz Behzadi.
U.S. Appl. No. 16/586,960, filed Sep. 28, 2019, Kambiz Behzadi.
U.S. Appl. No. 16/589,099, filed Sep. 30, 2019, Kambiz Behzadi.
U.S. Appl. No. 16/595,341, filed Oct. 7, 2019, Kambiz Behzadi.
U.S. Appl. No. 16/819,092, filed Mar. 14, 2020, Kambiz Behzadi et al.
U.S. Appl. No. 16/842,415, filed Apr. 7, 2020, Kambiz Behzadi.
U.S. Appl. No. 16/945,908, filed Aug. 2, 2020, Kambiz Behzadi et al.
U.S. Appl. No. 17/010,769, filed Sep. 2, 2020, Kambiz Behzadi et al.
U.S. Appl. No. 17/164,780, filed Feb. 1, 2021, Kambiz Behzadi.
U.S. Appl. No. 17/238,148, filed Apr. 22, 2021, Kambiz Behzadi.
U.S. Appl. No. 17/446,985, filed Sep. 7, 2021, Kambiz Behzadi.
U.S. Appl. No. 17/449,245, filed Sep. 28, 2021, Kambiz Behzadi.
U.S. Appl. No. 17/457,761, filed Dec. 6, 2021, Kambiz Behzadi.
U.S. Appl. No. 17/586,359, filed Jan. 27, 2022, Kambiz Behzadi.
U.S. Appl. No. 17/587,389, filed Jan. 28, 2022, Kambiz Behzadi.
U.S. Appl. No. 17/587,835, filed Jan. 28, 2022, Kambiz Behzadi et al.
U.S. Appl. No. 17/588,793, filed Jan. 31, 2022, Kambiz Behzadi.

\* cited by examiner

CONNECTIVE TISSUE GRAFTING

CROSS REFERENCE TO RELATED APPLICATIONS

This application is a Continuation-in-part of application Ser. No. 16/595,341 filed on Oct. 7, 2019; application Ser. No. 16/595,341 claims the benefit of U.S. Provisional Application 62/742,851 filed on Oct. 8, 2018; This application claims the benefit of U.S. Provisional Application 62/743,042 filed on Oct. 9, 2018, the contents of which are all hereby expressly incorporated by reference thereto in their entireties for all purposes.

FIELD OF THE INVENTION

The present invention relates generally to connective tissue grafts, repair of connective tissue ruptures, and more specifically, but not exclusively, to anterior cruciate ligament (ACL) repair.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Injury to connective tissue is common, particularly for those that are physically active. A common type of injury among certain sports and activities is the ACL injury. A healing potential of a ruptured ACL has been poor, and reconstruction of the ACL is often required for return to activity and sports. Various types of tendon grafts are used to reconstruct the ACL including allograft and autograft tissues. In general, bony tunnels are created in the tibia and femur and a variety of fixation devices are used to fix a graft that has been pulled into the knee joint, within the tunnels, to the tibia and femur. Various types of fixation are utilized to fix the graft to the bone tunnels. These fixation methods broadly categorized into cortical suspensory button fixation vs. aperture interference screw fixation.

Biology of Graft Healing

Tendon graft healing to a bone tunnel is one important factor affecting a success of a reconstructed ACL. An unruptured ACL attaches to bone through "direct" type insertion, which has a highly differential morphology including four specific zones: tendon, fibrocartilage, mineralized fibrocartilage, bone. This small 1 mm zone plays an important mechanical role in allowing progressive distribution of tensile loads from the tendon (ligament) to subchondral bone.

A reconstructed ACL may sometimes attach to bone in a different fashion called "indirect" type insertion, which has a significantly simpler ultrastructure. Indirect insertion involves anchoring of the tendon (ligament) into bone without the intervening fibrocartilaginous zones (non-mineralized and mineralized fibrocartilage). These fibers represent the type of anchoring that occurs between periosteum and bone referred to as Sharpey fibers. The design of this type of insertion allows for micro motion at the insertion site. It is not as efficient as the "direct" type insertion in allowing transition of mechanical forces from ligament to bone.

Problem—Suspensory Cortical Fixation Versus Aperture Interference Screw Fixation There are broadly two types of fixation: suspensory cortical fixation and aperture interference screw fixation. There is general consensus that there are advantages and disadvantages to each method of fixation.

Suspensory Cortical Fixation

FIG. 1 illustrates an example of suspensory cortical fixation 100. Fixation 100 includes an endobutton 105 supporting a graft 110 through a femoral tunnel 115 and a tibial tunnel 120.

Advantages of fixation 100 may include one or more of: (a) allows circumferential 360 degree contact between tendon and bone (maximized surface area contact for tendon to bone healing); (b) easier operation to perform; (c) less damage to bone and tendon at the time of surgery (less invasive—bone and tendon sparing); and (d) strong fixation.

Disadvantages of fixation 100 may include one or more of: (a) allows micro motion at the aperture, including (i) bungee effect (lengthwise micro motion), (ii) windshield wiper (side-to-side micro motion), and/or (iii) increased propensity for increased risk of poor healing such as tunnel widening; (b) low tendon to bone compression forces at the interface (less than ideal healing: always heals with "indirect" type healing (Sharpey Fibers, no transitional zone of mineralized and non-mineralized fibrocartilage).

Aperture Interference Screw Fixation

FIG. 2 illustrates an example of aperture interference screw fixation 200. Fixation 200 includes an interference screw 205 attached to a graft 210 that has the relationship illustrated between a tibial plateau 215 and Blumensaat's line 220 along with a tibial tunnel 225 wherein screw 205 is applied.

Advantages of fixation 200 may include one or more of: (a) significantly higher compression forces between tendon/bone interface (by an order of magnitude) relative to fixation 100; (b) rigid fixation with minimal or no micro motion in the bone tunnel; (c) ideal healing—graft 210 heals to bone by "direct" type insertion with much higher specialization of the tendon bone interface, allowing for progressive force transfer from tendon to bone (formation of the four zones: tendon, fibrocartilage, mineralized fibrocartilage, bone); and (d) faster healing.

Disadvantages of fixation 200 may include one or more of: (a) significant tissue damage to the graft and bone with interference screw fixation (weakening of the early fixation period—6 to 10 weeks); (b) loss of circumferential contact between tendon and bone, compromising maximal contact area between tendon and bone by at least 50%; and (c) inflammatory and cellular reaction to foreign body within the tunnel causing tunnel widening and cyst formation.

What is needed is a solution that improves connective tissue repair options while reducing disadvantages.

BRIEF SUMMARY OF THE INVENTION

Disclosed is a system and method for an improved connective tissue repair option that reduces disadvantages of conventional fixation options. The following summary of the invention is provided to facilitate an understanding of some of the technical features related to connective tissue preparation and repair systems and methods and is not intended to be a full description of the present invention. A full appreciation of the various aspects of the invention can be gained by taking the entire specification, claims, drawings, and abstract as a whole. The present invention is applicable to other connective tissue repair systems and methods in addition to repair of an anterior cruciate ligament (ACL) injury including other connective tissue repairs using a suspensory-type or aperture-type solution.

An embodiment may include a graft platform (e.g., a table or stage) that is specially configured for pre-repair preparation of a connective tissue graft. This structure temporarily compresses and/or tensions (e.g., stretches) the connective tissue graft which temporarily reduces its outer perimeter (e.g., for a circular graft this may refer to a radius/circumference of the graft) appropriately in advance of installation. After installation, the connective tissue graft naturally expands towards its original unreduced perimeter in situ which may apply high compressive forces at a ligament/bone interface within bone tunnels through, or into, which the reduced graft had been installed.

An embodiment for a graft platform includes a graft compression system. A graft compression system may be implemented in many different ways—it may include a support for a pair of stages that may be coupled together via an optional controllable separation mechanism that controls a distance between these stages. Each stage may include a gripping system that provides compression to reduce and/or profile the perimeter. The compression system may include one or both of these compressive mechanisms: (a) grip and stretch, and/or (b) grip and squeeze.

This may increase the possibility of the more natural "direct-type" tendon to bone healing which decreases risks of repair failures that arise from "indirect-type" healing.

This may allow a surgeon to use repair procedures that preserve more bone. These procedures often include preparing the tunnels in the bone and allowing for use of a reduced perimeter graft allows the surgeon to prepare smaller radius tunnels or to improve graft repair strength of conventionally sized tunnels, at the surgeon's discretion. More options allow the surgeon to provide better customized solutions to the patience.

An embodiment of the present invention may include a graft-preparation table that includes a pair of relatively moveable stages (e.g., a distance between these stages is variable). Each stage may be provided with a compressive structure that secures the graft. The stage may compress the graft by direct compression through application of force(s) on the perimeter and/or indirect compression by tensioning the graft such as by stretching the graft through pulling.

Method and Apparatus Claims for creation of Non-cylindrical, asymmetric, conical, frustum like, profiled, curvilinear tunnels for ACL reconstruction (as well as other ligaments in other joints), in which a natural mechanical resistance to pull out is produced for a decompressing and/or expanding compressed connective tissue graft by the inherent asymmetric shape of the tunnel (A) using existing 3D sculpting or existing robotic techniques and/or new bone preparation techniques.

Method and Apparatus for creation of ACL (PCL, MPFL, MCL, LCL) ligament bone tunnels without the use of a pre-determined guide wire and over drilling technique.

Method and Apparatus for correlating precisely or matching precisely (e.g., to within 1 mm) the length of ACL graft with the length of bony tunnels+intra articular ACL, when using robotic or 3D bone sculpting techniques, instead of guide wire and over drill techniques.

Method and Apparatus for producing the environment which allows a "biologic press fit" fixation, where high tendon-bone interface forces are achieved with a passively or actively decompressing/expanding (previously compressed) ACL graft, which may be used with or without suspensory cortical fixation and with or without mechanical foreign body (e.g., screw-less) fixation.

Method and Apparatus for delivery of various biological growth factors within a compressed ACL graft to enhance tendon bone healing with direct type and/or indirect type healing at the interface (angiogenesis and osteogenesis) with or without suspensory cortical fixation and with or without mechanical foreign body (e.g., screw-less) fixation.

Method and Apparatus for embedding sensors (biologic and/or electronic) within the substance of ACL (and other ligament) grafts to assess (A) intra-tunnel interface forces (pressures), in order to determine if/when interface forces are adequate (high) enough for direct type and/or indirect type healing (B) intra-articular ligament tensile and shear forces (within the notch) to determine failure mechanisms and maximal load to failure in the case of re injury or re rupture.

Method and Apparatus for pre-compressing and shipping pre-compressed connective tissue graft, including use of a sheathing system having one or more layers, those layers may include: structural elements to maintain compression until pre-operative preparation; time-delaying materials/construction for manipulation of active/passive decompression/expansion; inclusion of biologic sensors; and/or inclusion of biologic growth/healing/bone or tissue conditioning factors to promote a desired outcome with the installation of the decompressing/expanding compressed graft within a prepared bone tunnel.

Method and Apparatus for embedding a set of one or more prosthetic elements inside a connective tissue graft (conventional or pre-compressed) and securing/deploying/installing a prosthetically-enhanced natural connective tissue within a prepared bone tunnel for fixation, the fixation may include the passive/active decompression/expansion of a pre-compressed prosthetically-enhanced connective tissue graft, the enhancement including a set of one or more natural, synthetic, and/or hybrid materials having a material property different from natural connective tissue.

Method and Apparatus for deploying expansion structures within a natural connective tissue graft, initiating and manipulating enlargement of those expansion structures to actively expand the natural connective tissue graft; and including a prosthetic element as part of or cooperative with the deployed expansion structures.

An apparatus for decreasing a diameter of a unit of a compressible connective tissue, including a compressor configured to receive the unit within a diameter-decreasing structure, the compressor including an actuator coupled to the diameter-decreasing structure with the actuator configured to operate the compressor to decrease a diameter of the compressible connective tissue using a diameter-decreasing action of the compressor; a control, coupled to the actuator, initiating the diameter-decreasing action.

A connective tissue unit for installation into a prepared bone aperture, the connective tissue having a first diameter, the prepared bone aperture having a second diameter smaller than the first diameter, including a compressed connective tissue unit having a compressed diameter smaller than the second diameter and configured to engage within the prepared bone aperture for an engaged connective tissue unit and wherein the engaged connective tissue unit is configured to increase the compressed diameter after engagement within the prepared bone aperture to at least match the second diameter.

A method for decreasing a diameter of a unit of a compressible connective tissue, including receiving the unit within a diameter-decreasing structure of a compressor, the compressor including an actuator coupled to the diameter-decreasing structure with the actuator configured to operate the compressor to decrease a diameter of the compressible connective tissue using a diameter-decreasing action of the compressor; and operating the actuator to initiate the diameter-decreasing action.

A method for installing a connective tissue graft into a prepared bone tunnel, including compressing the connective tissue graft producing a compressed tissue graft having a diameter smaller than a diameter of the prepared bone tunnel; installing the compressed tissue graft within the prepared bone tunnel producing an installed tissue graft; and decompressing the installed tissue graft within the prepared bone tunnel producing a decompressed tissue graft having a decompressed diameter at least equal to the diameter of the prepared bone tunnel.

A method for preparing a bone tunnel in a portion of bone, the bone tunnel configured to receive an installation of a ligament, including operating a bone-shaping implement configured to produce a non-cylindrical bone tunnel having a bone tunnel profile; and shaping the portion of bone using the bone-shaping implement to create a non-cylindrical bone tunnel including the bone tunnel profile.

A connective tissue installation system, including a bone tunnel prepared in a portion of bone, the bone tunnel including an external opening and a cavity in the portion of bone with the cavity accessed through the external opening; and a connective tissue unit secured within the bone tunnel using a biologic press fit fixation responsive to an in situ expansion of at least a portion of the connective tissue unit within the bone tunnel.

A connective tissue graft for an installation within a bone tunnel having an external opening into a cavity prepared in a portion of a bone, including a connective tissue unit having a compressed portion with a diameter smaller than a diameter of the external opening; wherein the compressed portion is configured for an in situ decompression or an in situ expansion within the bone tunnel after installation wherein the decompression or the expansion is configured for a biologic press fit fixation of the connective tissue unit within the bone tunnel.

Method and Apparatus Claims for creation of Non-cylindrical, asymmetric, conical, frustum like, profiled, curvilinear tunnels for ACL reconstruction (as well as other ligaments in other joints), in which a natural mechanical resistance to pull out is produced for a decompressing and/or expanding compressed connective tissue graft by the inherent asymmetric shape of the tunnel (A) using existing 3D sculpting or existing robotic techniques and/or new bone preparation techniques.

Method and Apparatus for creation of ACL (PCL, MPFL, MCL, LCL) ligament bone tunnels without the use of a pre-determined guide wire and over drilling technique, such as without drilling over a previously placed guide wire with a cannulated drill/drill bit.

Method and Apparatus for correlating precisely or matching precisely (e.g., to within 1 mm) the length of ACL graft with the length of bony tunnels+intra articular ACL, when using robotic or 3D bone sculpting techniques, instead of guide wire and over drill techniques, such as techniques based on an inherent ability of navigation and robotic methods using 3D scanning or morphing technology to pre-operatively or intra-operatively determine an exact intra-articular length of ACL graft and bone tunnels.

Method and Apparatus for producing the environment which allows a "biologic press fit" fixation, where high tendon-bone interface forces are achieved with a passively or actively decompressing/expanding (previously compressed) ACL graft, which may be used with or without suspensory cortical fixation and with or without mechanical foreign body (e.g., interference screw) fixation.

Method and Apparatus for delivery of various biological growth factors within a compressed ACL graft to enhance tendon bone healing with direct type and/or indirect type healing at the interface (angiogenesis and osteogenesis) with or without suspensory cortical fixation and with or without mechanical foreign body (e.g., interference screw) fixation.

Method and Apparatus for embedding sensors (biologic and/or electronic) within the substance of ACL (and other ligament) grafts to assess (A) intra-tunnel interface forces (pressures), in order to determine if/when interface forces are adequate (high) enough for direct type and/or indirect type healing (B) intra-articular ligament tensile, shear, and/or torsional forces (within the notch) to determine failure mechanisms and maximal load to failure in the case of re injury or re rupture.

Method and Apparatus for pre-compressing and shipping pre-compressed connective tissue graft, including use of a sheathing system having one or more layers, those layers may include: structural elements to maintain compression until pre-operative preparation; time-delaying materials/construction for manipulation of active/passive decompression/expansion; inclusion of biologic sensors; and/or inclusion of biologic growth/healing/bone or tissue conditioning factors to promote a desired outcome with the installation of the decompressing/expanding compressed graft within a prepared bone tunnel.

Method and Apparatus for embedding a set of one or more prosthetic elements inside a connective tissue graft (conventional or pre-compressed) and securing/deploying/installing a prosthetically-enhanced natural connective tissue within a prepared bone tunnel for fixation, the fixation may include the passive/active decompression/expansion of a pre-compressed prosthetically-enhanced connective tissue graft, the enhancement including a set of one or more natural, synthetic, and/or hybrid materials having a material property different from natural connective tissue.

Method and Apparatus for deploying expansion structures within a natural connective tissue graft, initiating and manipulating enlargement of those expansion structures to actively expand the natural connective tissue graft; and including a prosthetic element, such as described herein, as part of, or cooperative with, the deployed expansion structures.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 13 illustrates pre-expansion of a compressed ACL graft;

FIG. 14 illustrates a post-expansion of the compressed ACL graft;

FIG. 15 illustrates pre-expansion of a compressed ACL graft;

FIG. 16 illustrates a post-expansion of the compressed ACL graft;

DETAILED DESCRIPTION OF THE INVENTION

Figure 1:
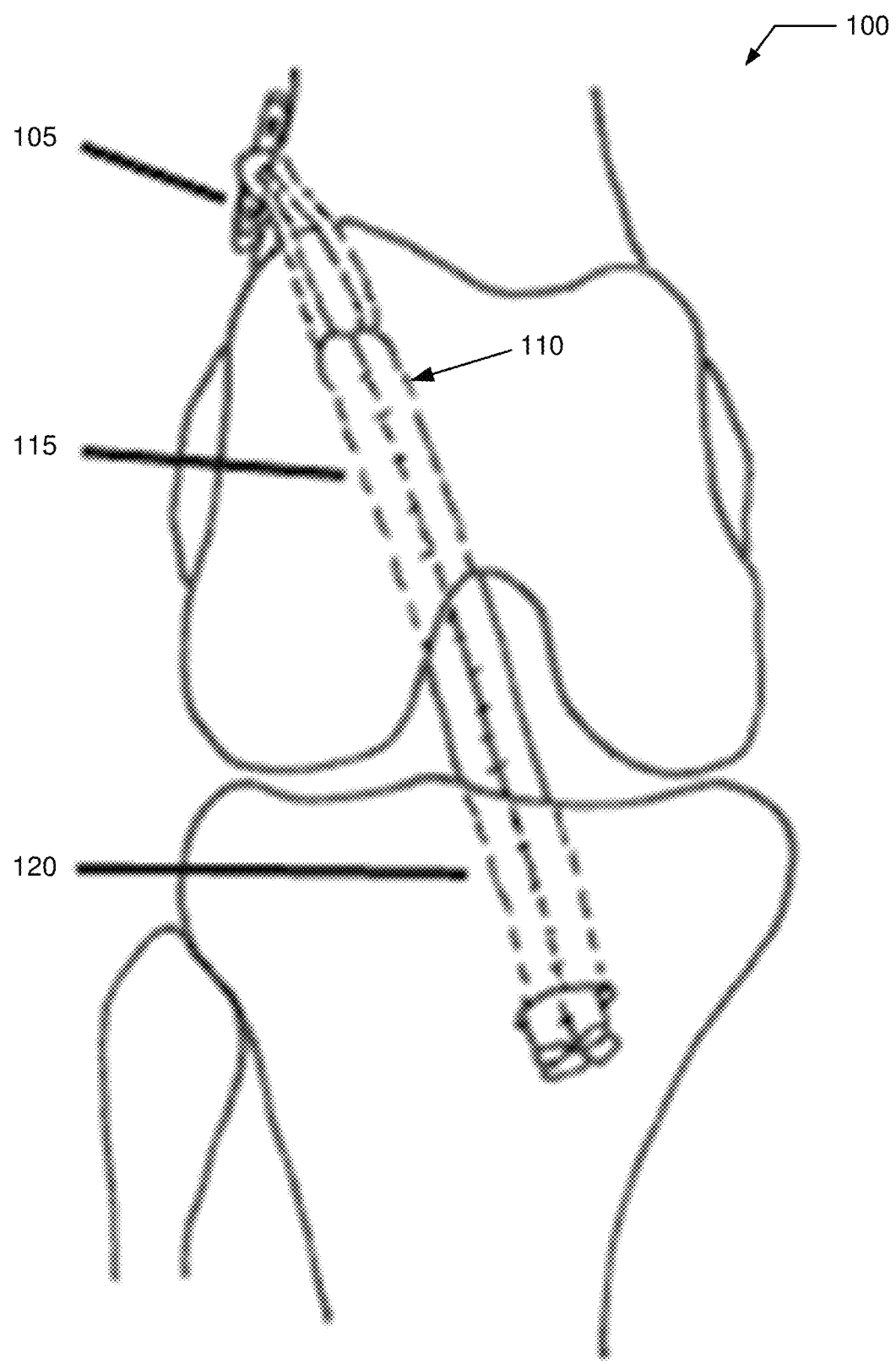
FIG. 1 illustrates an example of suspensory cortical fixation.
Figure 2:
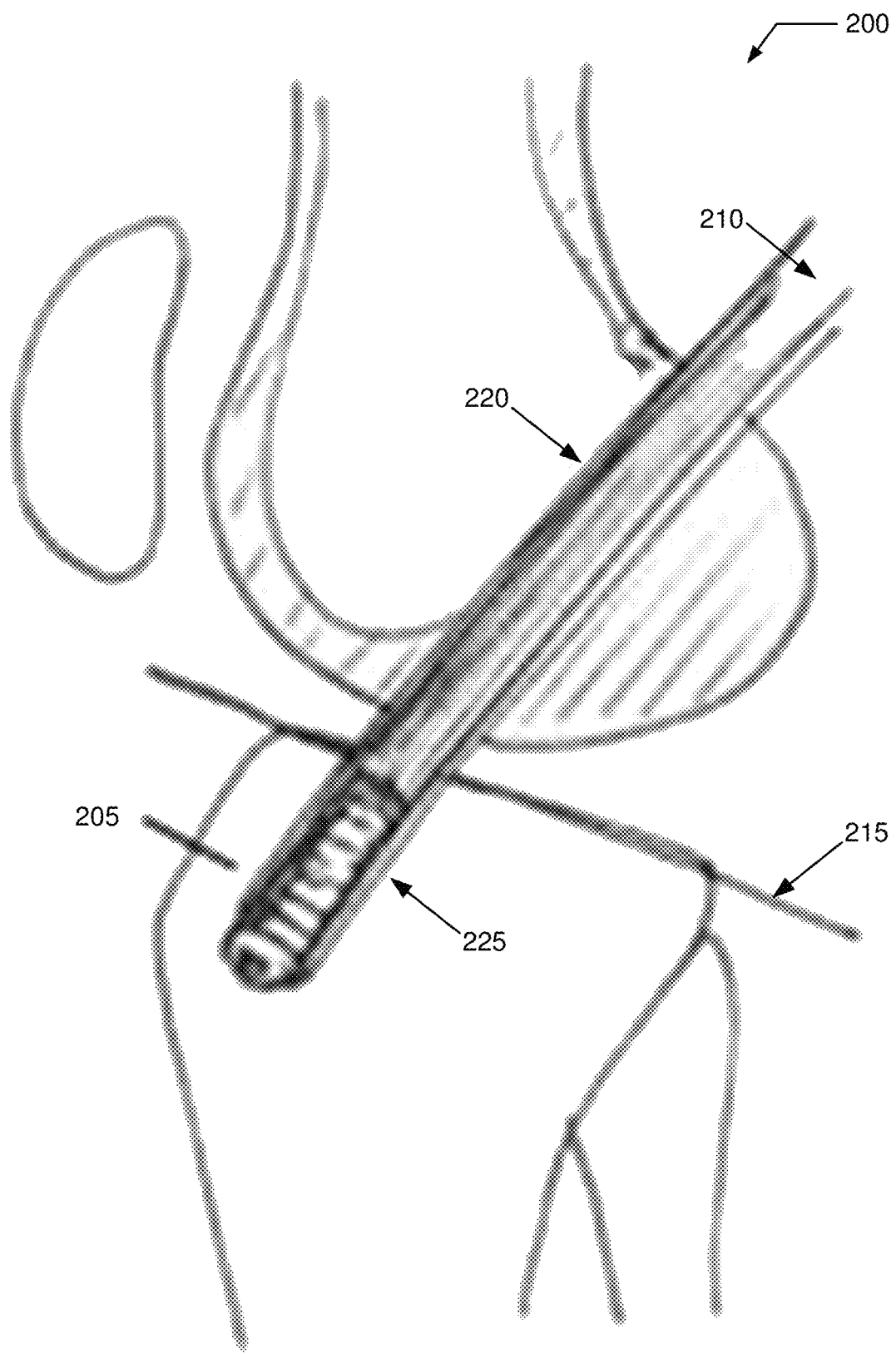
FIG. 2 illustrates an example of aperture interference screw fixation.

Embodiments of the present invention provide a system and method for an improved connective tissue repair option that reduces disadvantages of conventional fixation options. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, the term "compress" or "compression" with respect to a compressible connective tissue unit means a decrease in a diameter of the compressible connective tissue unit whether the decrease occurs actually through a compression or otherwise such as a tensioning and/or a torsioning or other manipulation or operation on the tissue unit.

The present invention may be useful for a wide-range of connective tissue grafts used in a wide-range of repair techniques. With this understanding, to simplify the discussion a particular type of graft used in a particular type of repair technique: an ACL graft used for repair of a ruptured ACL.

The knee is a simple hinge joint at the connection point between the femur and tibia bones. It is held together by several important ligaments. The most important of these to the knee's stability is the Anterior Cruciate Ligament (ACL). The ACL attaches from the front part of the tibia to the back part of the femur. The purpose of this ligament is to keep the tibia from sliding forward on the femur. For this reason, the ACL is most susceptible to injury when rotational or twisting forces are placed on the knee. Although this can happen during a contact injury many ACL tears happen when athletes slow down and pivot or when landing from a jump.

After the ACL is torn the knee is less stable and it becomes difficult to maintain a high level of activity without the knee buckling or giving way. It is particularly difficult to perform the repetitive cutting and pivoting that is required in many sports.

Regardless of how the ACL is torn a physician will work with their patient to determine what the best course of treatment will be. In the case of an isolated ACL tear (no other ligaments are involved) the associated pain and dysfunction may often be successfully treated with rest, anti-inflammatory measures, activity modification and Physical Therapy. After the swelling resolves and range of motion and strength is returned to the knee a decision can be made as to how to proceed. Many people elect to use a sports brace and restrict their activity rather than undergo surgery to reconstruct the ACL. When a non-surgical approach is taken the patient must understand that it is imperative that she or he maintain good strength in her or his leg and avoid sports or activities that require pivoting or cutting. When conservative measures are unsuccessful in restoring function the patient and their physician may elect to have the torn ligament reconstructed.

ACL reconstruction surgery is not a primary repair procedure. This means that the ligament ends cannot simply be sewn back together. The new ACL must come from another source and grafted into place in the knee. There are a few different options as to what tissue is used for the ACL graft (three most common sources include patella tendon, hamstring tendon, and cadaver tendon) and each patient should consult with his or her surgeon to determine the best choice. During the procedure a set of tunnels are drilled within the tibia and femur and the new ACL graft is passed into these tunnels and anchored into place. Some or all of this anchoring, in embodiments of the present invention, occur by use of an in situ decompression of a compressed end portion of the ACL graft within a prepared tunnel.

The ACL graft includes a highly hydrated and compressible tissue. As observed by applicant, a diameter of a typical ACL graft may be compressed, for example by up to 2 to 4 millimeters, with special techniques that can be employed just prior to installation. The native ACL graft can be manipulated (e.g., compressed and/or stretched) to produce a manipulated ACL graft that has a smaller diameter than the native ACL graft. For this discussion, the native ACL graft may include a 10-millimeter diameter while the manipulated ACL graft may include a 7-millimeter diameter.

The manipulated ACL may subsequently be implanted at a significantly compressed diameter than its original form (i.e. 7 mm instead of 10 mm) and allowed to expand, in a delayed fashion, within bone tunnels formed and used during the repair procedure, producing high contact forces at an interface between the manipulated ACL graft and the bone of the tunnel (e.g., a tendon/bone interface).

This repair may be accomplished with all the positive attributes of suspensory cortical and aperture fixation and without any of the negative attributes of the two fixation methods.

This method of "biological press fit" fixation does not have the negative attributes of interference screw fixation including: without the use of an interference screw and its attendant negative attributes including: (i) damage to the graft and bone; (ii) loss of circumferential contact; and (iii) foreign material within the tunnels causing late inflammatory and destructive reactions in bone. Similarly, the "biological press fit" fixation dos not have the negative attributes of suspensory cortical fixation including: (i) micro motion at the aperture causing bungee (lengthwise micro motion) and windshield wiper (side-to-side micro motion) effects, (ii) increasing risk of tunnel widening; and (iii) low tendon-bone interface compression forces leading to "indirect" type healing (Sharpey Fibers, with no transitional zone of mineralized and non-mineralized fibrocartilage, for specialized transfer of force).

An embodiment of the present invention may allow all the positives attributes of both suspensory cortical and aperture fixation. "Biologic press fit" fixation may embody all the positive attributes of suspensory cortical fixation including: (i) circumferential 360-degree contact between tendon and bone (maximized surface area contact for tendon to bone healing); (ii) easier operation to perform; (iii) less damage to bone and tendon at the time of surgery (less invasive—bone and tendon sparing); (iv) strong fixation. "Biological press fit" fixation similarly may embody all the positive attributes of aperture fixation including: (i) significantly higher compression forces between tendon/bone interface; (ii) rigid fixation with minimal or no micro motion in the bone tunnel; (iii) ideal healing—by "direct" type insertion with specialization of the tendon bone interface, allowing for progressive force transfer from tendon to bone (formation of the four zones: tendon, fibrocartilage, mineralized fibrocartilage, bone); and (iv) faster healing.

The combination of factors noted above are believed to allow high interference forces that may be obtained soon after implantation (including decompression of manipulated ACL graft within a portion of a one tunnel), these interference forces due to the in situ decompression of the manipulated ACL graft, without interference of foreign material within the tunnels.

Some embodiments may include application of one or more remotely readable biological sensors to the manipulated ACL graft. The sensors may, for example, include a capacity to measure contact forces at the tendon/bone interface of the expanding manipulated ACL graft within a tunnel. These sensors may be applied to the ACL graft as part of the preparation or provided to the surgeon prior to compression. There may be various uses of this/these sensor(s), in order to assess compressive forces produced at the tendon/bone junction at time zero and over defined periods of time.

Figure 3:
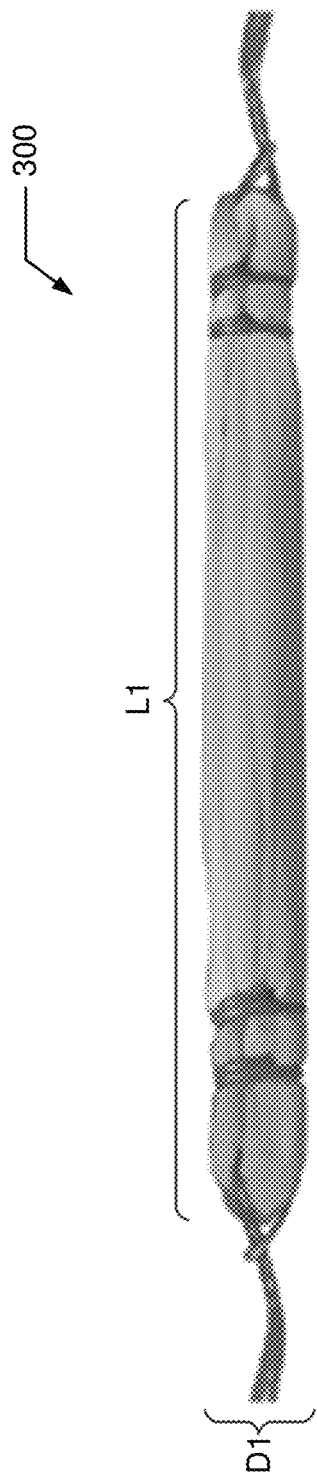
FIG. 3 illustrates an example of a native connective tissue graft.

FIG. 3 illustrates an example of a native connective tissue graft 300. Graft 300 is provided with predetermined general dimensions, including a length L1 and a diameter D1. For example, for an ACL reconstruction, graft may have L1 about 90-180 millimeters (determined by patient anatomy) and D1 about 10 millimeters.

Figure 4:
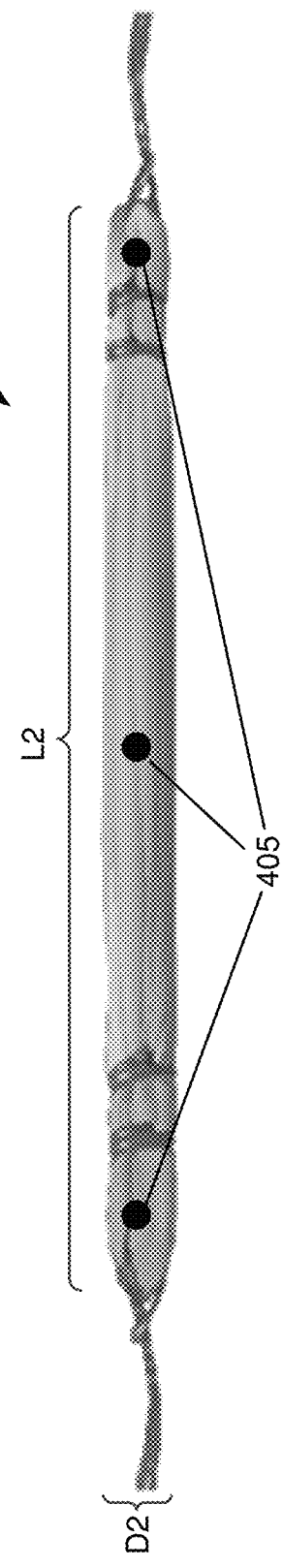
FIG. 4 illustrates an example of a compressed connective tissue graft that may result from a pre-operative compressive treatment of the native connective tissue graft of FIG. 3.

FIG. 4 illustrates an example of a compressed connective tissue graft 400 that may result from a pre-operative compressive treatment of native connective tissue graft 300. Graft 400 includes a length L2 that may be about greater than or equal to L1 and further includes a diameter D2 that is less than D1. One or more remotely readable biologic sensors 405 may be included with graft 400.

Sensor(s) 405 may be included as part of graft 300 (pre-manipulation) or may be applied to a surface of graft 400 or bulk-integrated into a body of graft 400 as part of, or attendant to, pre-reconstruction preparation of graft 400.

Sensor(s) 405 may be used for different purposes to assess a quality of various aspects of the reconstruction procedure. For example, a compression reading at one or more interfaces between one or more end portions of graft 400 within the bone tunnel into which graft 400 was installed may be used to measure healing and fixation. A sensor 405 disposed outside of a tunnel between the femur and the tibia may include a stress-strain gauge to understand the potentially rupturing forces that the patient applies to the reconstructed ACL graft (after surgery) in the course of their activities. Readings may be taken immediately after installation and then at various subsequent times to assess a magnitude of the graft/bone interface at that/those portion(s). The readings may indicate that healing is progressing (and some metric of how well the healing has progressed), healing has largely completed past a predetermined threshold, or that there may be some complication in the healing process.

Figure 5:
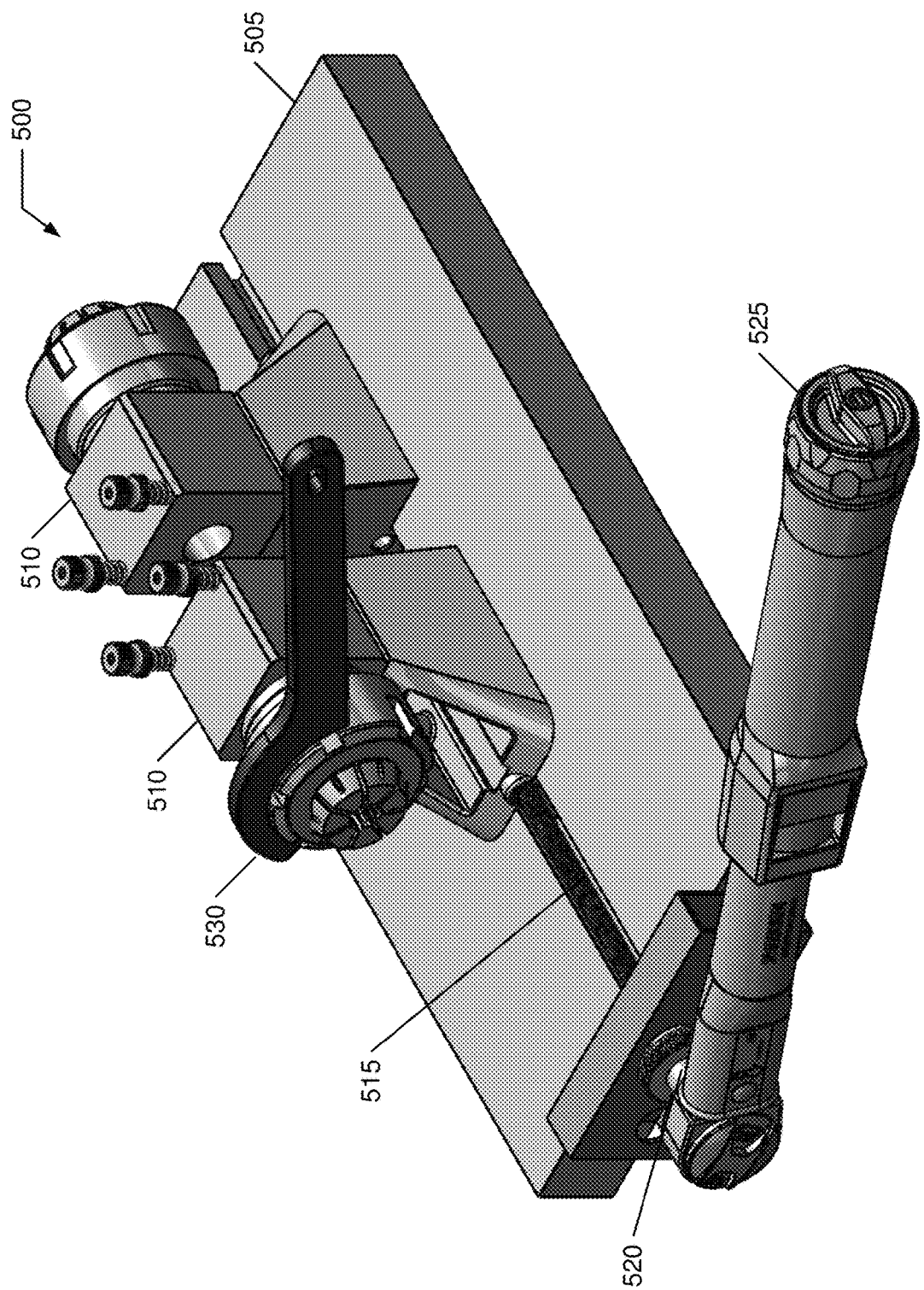
FIG. 5 illustrates a perspective view of a graft platform.

FIG. 5 illustrates a perspective view of a graft platform 500. Platform 500 may include a table 505 supporting a pair of moveable sleeve housings 510. Housings 510 move relative to each other (one or both housings 510 may move). Movement may be controlled by a drive rod 515 having a knob 520. Knob 520 may be turned using a torque wrench 525 to understand how much force is being used to separate housings 510. One may want to be sure that not too small or too large force is used in separating housings 510 as this influences an amount of tension/deformation to any graft being manipulated by platform 500.

Each housing 510 supports a graft sleeve that defines a conical internal sleeve structure into which a collet chuck is introduced and upon which a collet nut is threaded over the collet chuck within the internal sleeve structure using complementary threaded portions of an end of the graft sleeve. A wrench 530 may be used to tighten the collet nut onto the graft sleeve. One or more suture holders may be used to support graft 300 when initially installed into graft platform 500. For purposes of this illustration FIG. 5, sleeve housings 510 are shown facing away from each, while in actual operation housings 510 are reversed as illustrated in FIG. 6.

Figure 6:
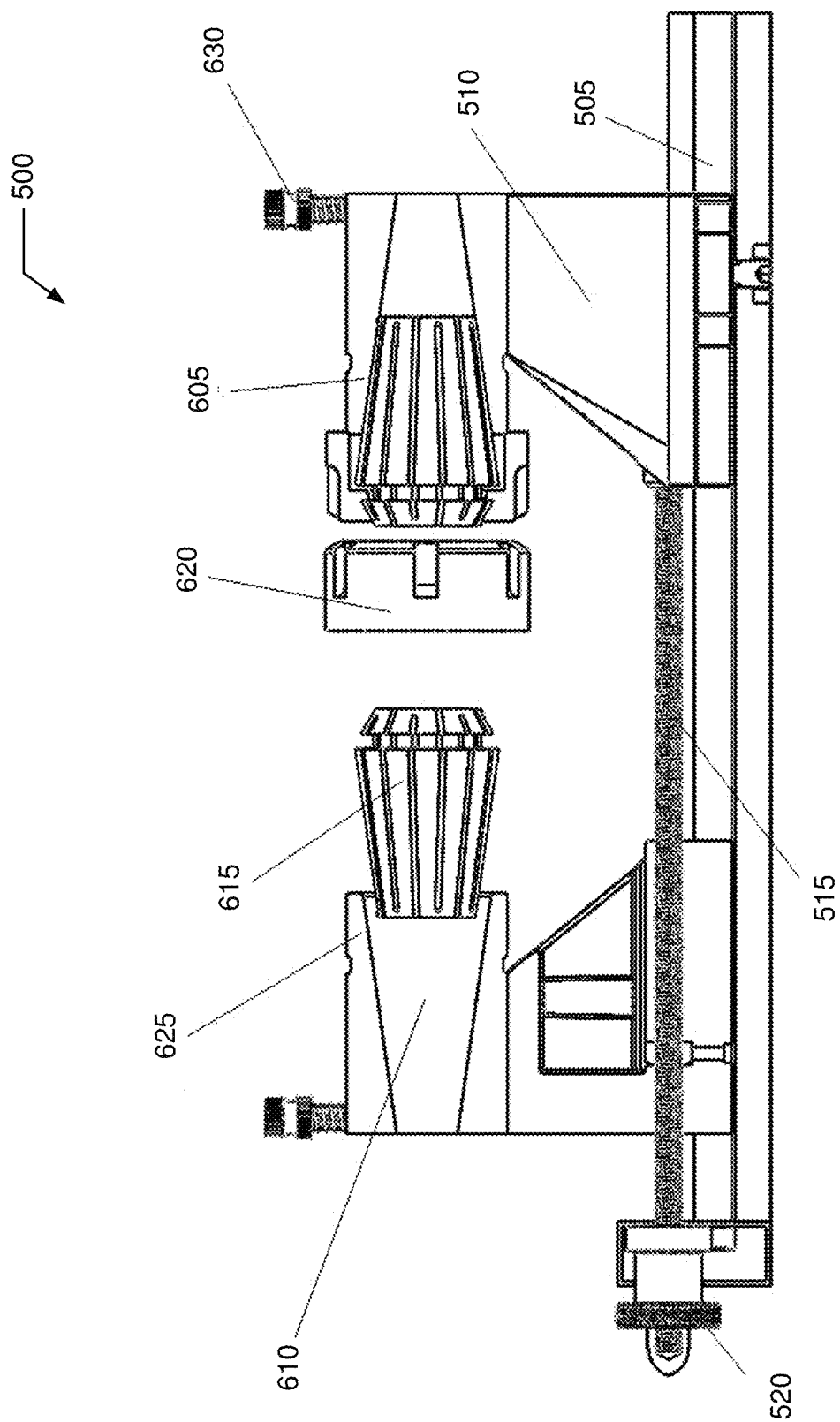
FIG. 6 illustrates a side view of the graft platform of FIG. 5 with repositioned stages.

FIG. 6 illustrates a side view of graft platform 500 with repositioned housings 510 to face each other. Platform 500 includes a graft sleeve 605 coupled to housing 510. Each graft sleeve 605 defines a conical internal sleeve structure 610 into which a collet chuck 615 is positioned. A threaded collet nut 620 is positioned over collet chuck 615 and is installed onto sleeve 605 by use of a threaded end 625 of graft sleeve 605. Each graft sleeve 605 includes one or more suture holders 630.

In operation, graft 300 is installed into graft platform 500 with each sleeve 605 gripping one end. There are different possible operational modes for graft platform 500 to compress graft 300 and produce graft 400, depending upon the procedure agreed upon by the patient and surgeon.

Graft platform 500 may compress some or all of graft 300 by applying equal lateral compressive forces along its length (by appropriate positioning and tightening of collet chucks 625 into structures 610 using nut 620 and/or separating housings 510 from each other using knob 520 to rotate rod 515.

Figure 7:
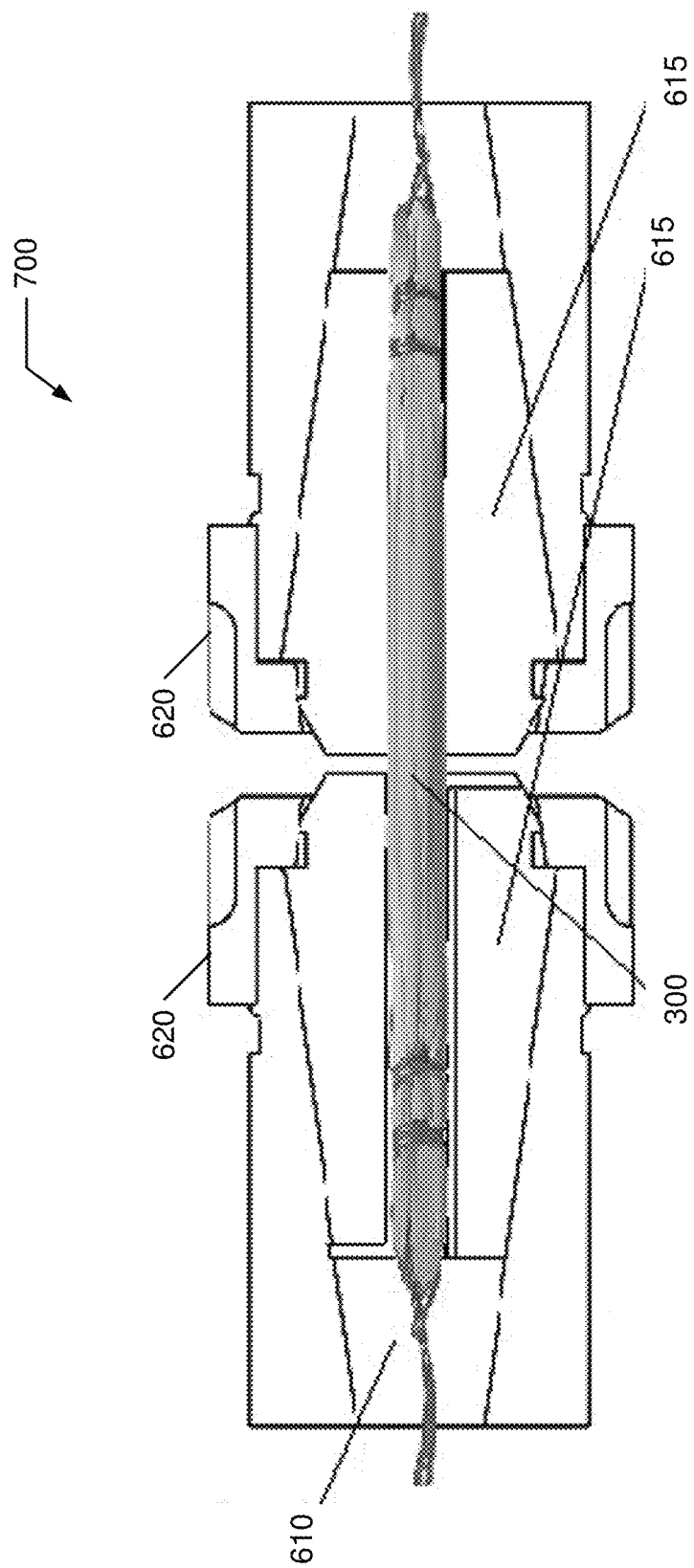
FIG. 7 illustrates a sectional view of a pair of collets gripping the native connective tissue graft of FIG. 3.

FIG. 7 illustrates a sectional view 700 of a pair of collet chucks 615 of platform 500 gripping native connective tissue graft 300 by being forced into structure 610. Each collet chuck 615 includes a longitudinal tunnel having a variable diameter. That diameter is greatest when it is initially installed into structure 610. As nut 620 is tightened, such as with wrench 530, the corresponding chuck 615 is forced deeper into conical structure 610 which decrease the diameter of the longitudinal tunnel. Decreasing the longitudinal tunnel while a portion of graft 300 is installed is one manner by which lateral compressive forces may be applied to that portion of graft 300 (which decreases the diameter of that portion of graft 300). Chuck 615 may be designed to have a physically determined minimum diameter to help ensure that graft 300 is not excessively compressed.

Figure 8:
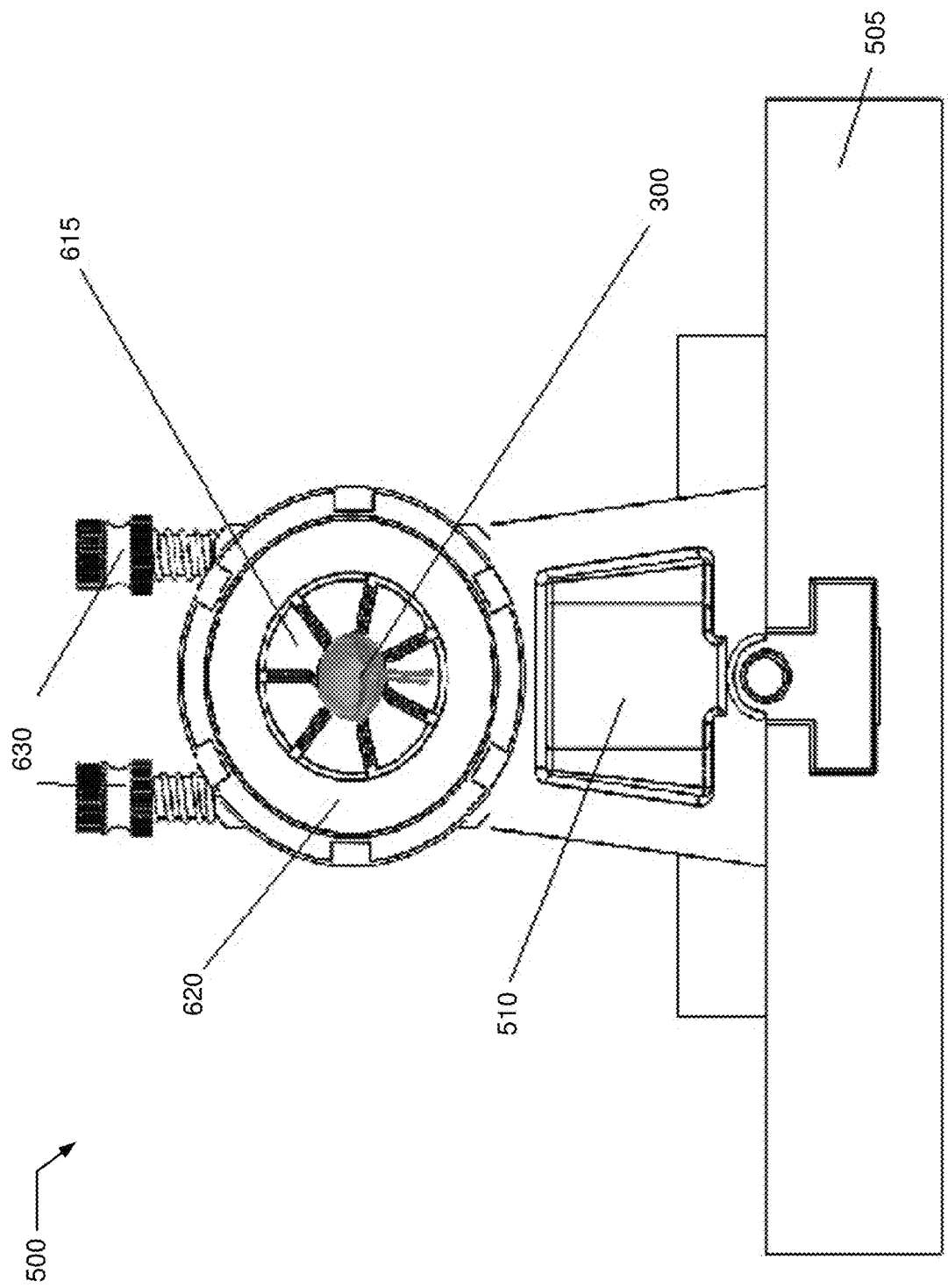
FIG. 8 illustrates an end view of FIG. 7.

FIG. 8 illustrates an end view of FIG. 7 in the context of platform 500. In this view, chuck 615 is in the initial or "open" state. Each collet chuck includes a number of tabs arrayed around the longitudinal tunnel, and in the open state, these tabs are separated. Forcing chuck 615 into structure 610 by turning nut 620 moves these tabs closer together to narrow the longitudinal tunnel and to thereby compress graft 300.

Figure 9:
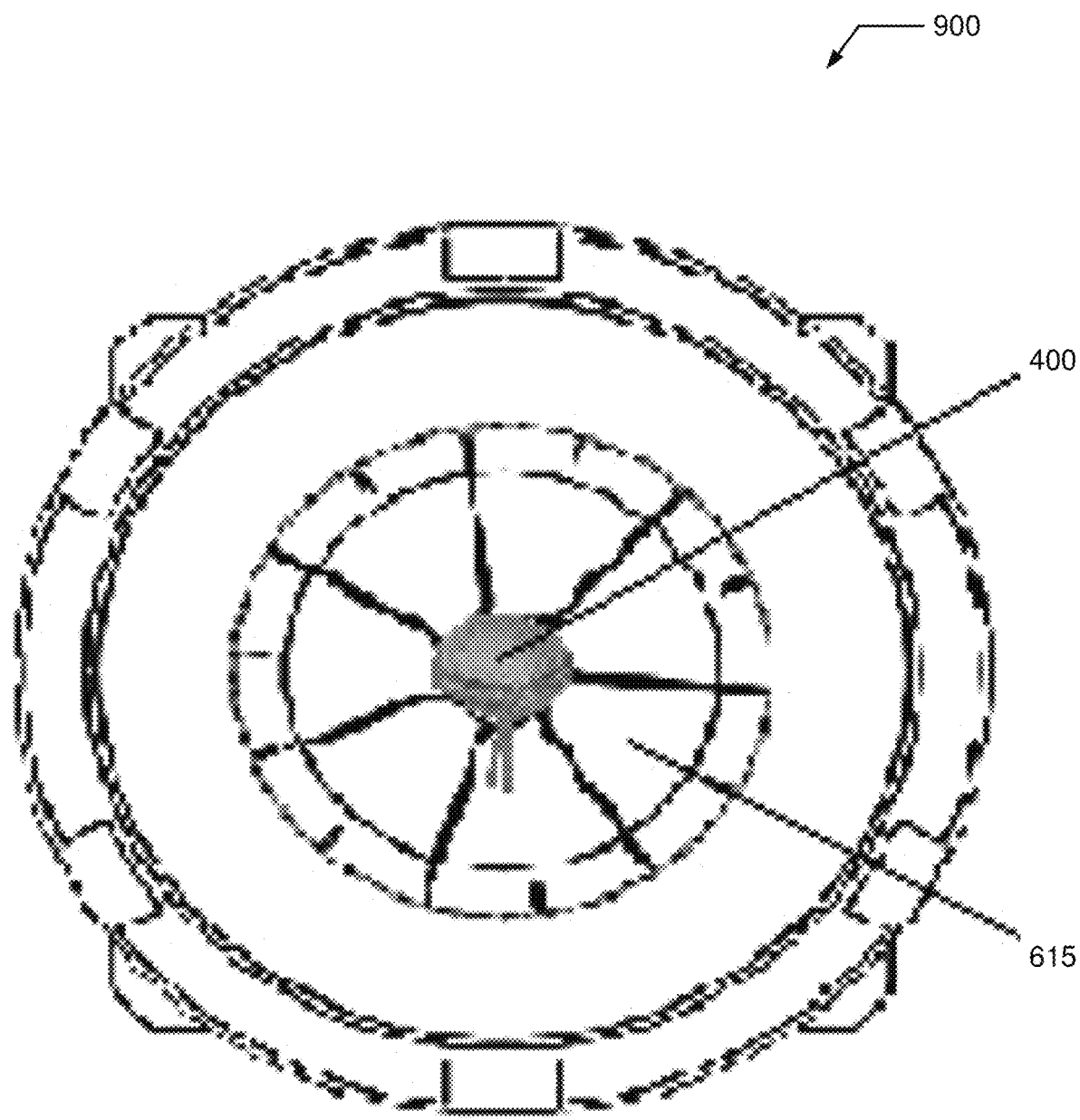
FIG. 9 illustrates an end view similar to FIG. 8 but after lateral compression to produce the compressed connective tissue graft of FIG. 4.

FIG. 9 illustrates an end view 900 similar to FIG. 8 but after lateral compression (e.g., longitudinal tunnel of chuck 615 closed) to produce compressed connective tissue graft 400. In FIG. 9 the tabs of chuck 615 are closed/touching which produces the smallest diameter longitudinal tunnel. This is in contrast to FIG. 8 where the tabs are separated and define a larger diameter longitudinal tunnel.

Figure 10:
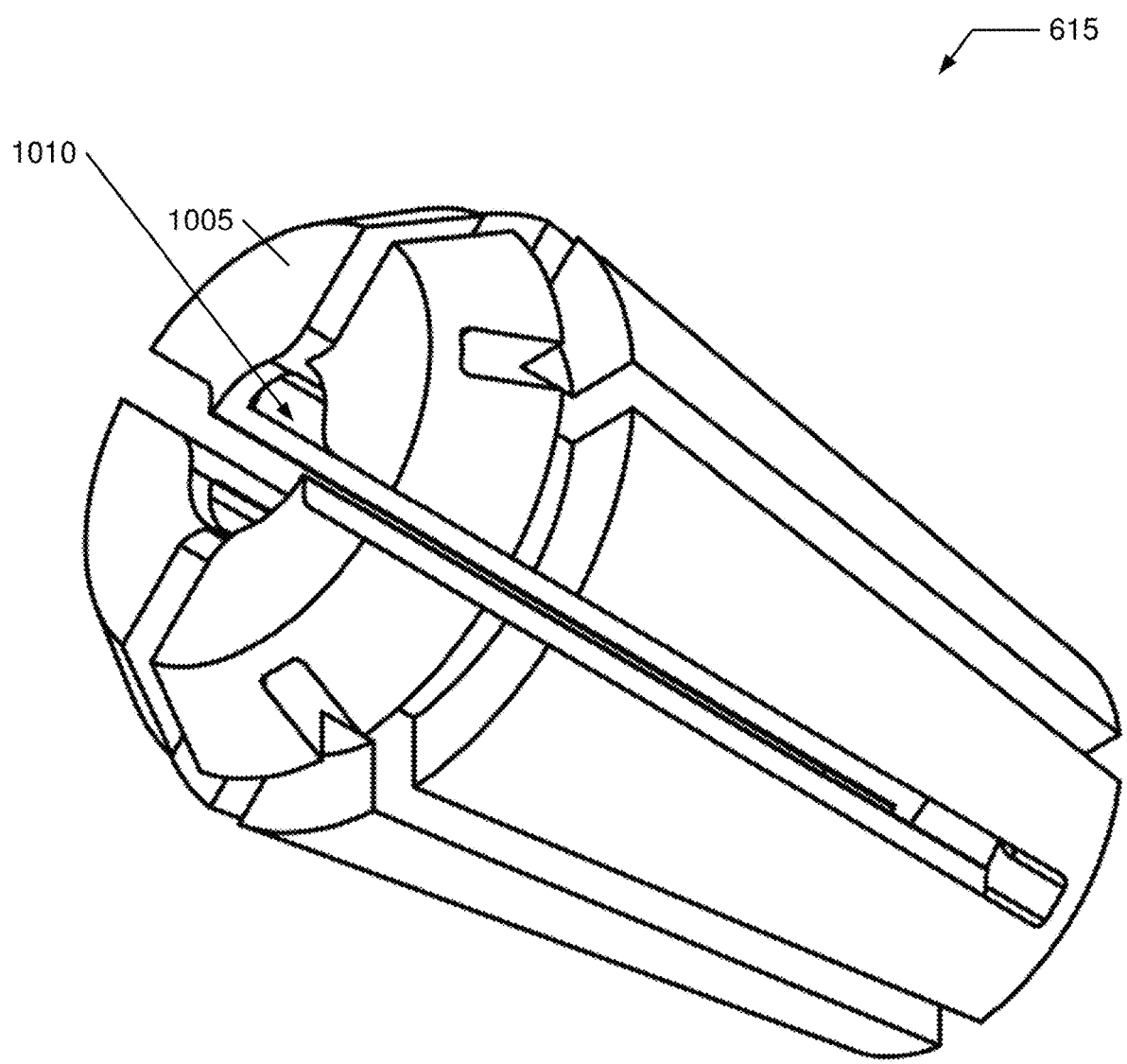
FIG. 10 illustrates a perspective view of a collet of the graft platform.
Figure 11:
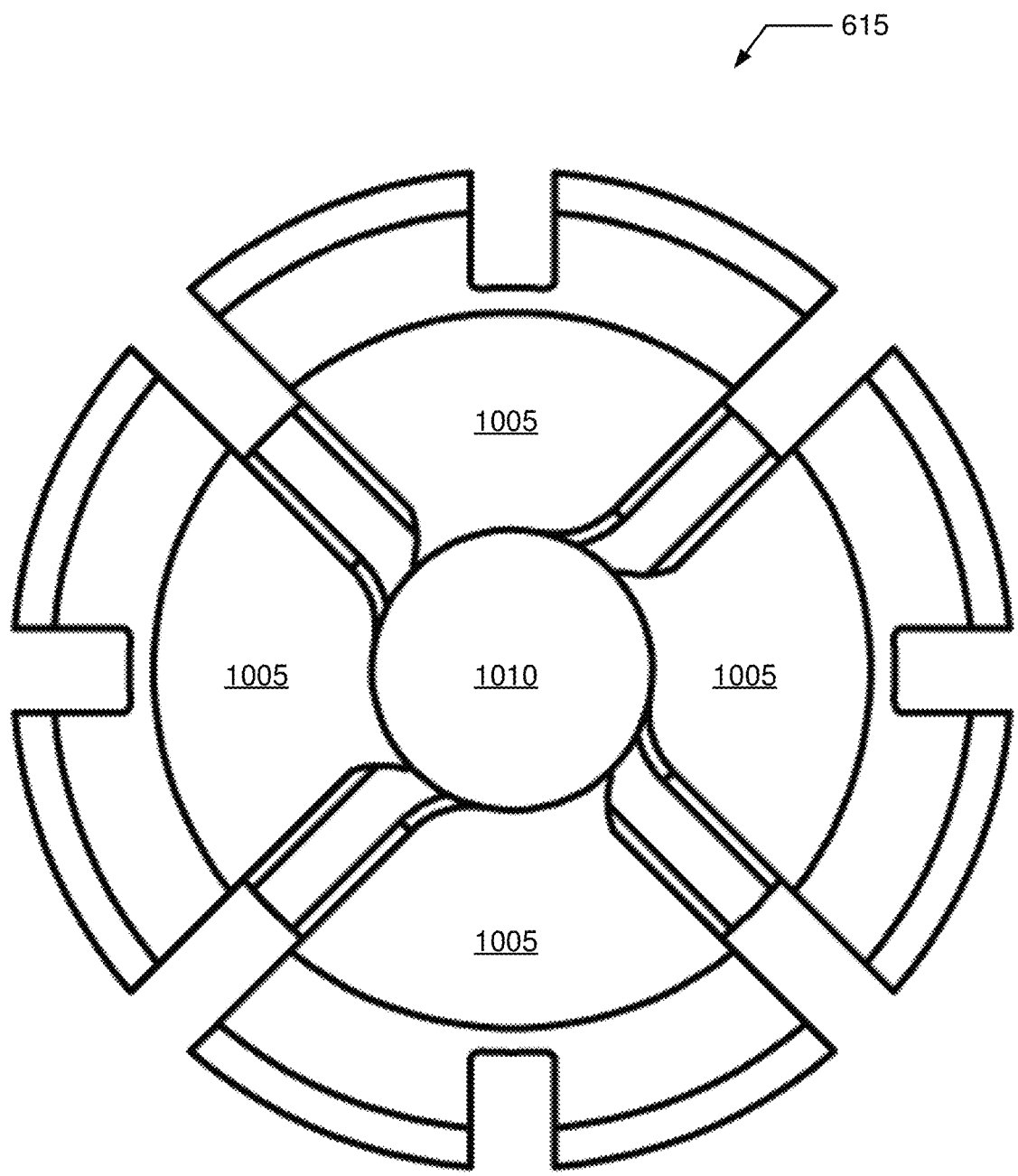
FIG. 11 illustrates an end view of the collet of FIG. 10.
Figure 12:
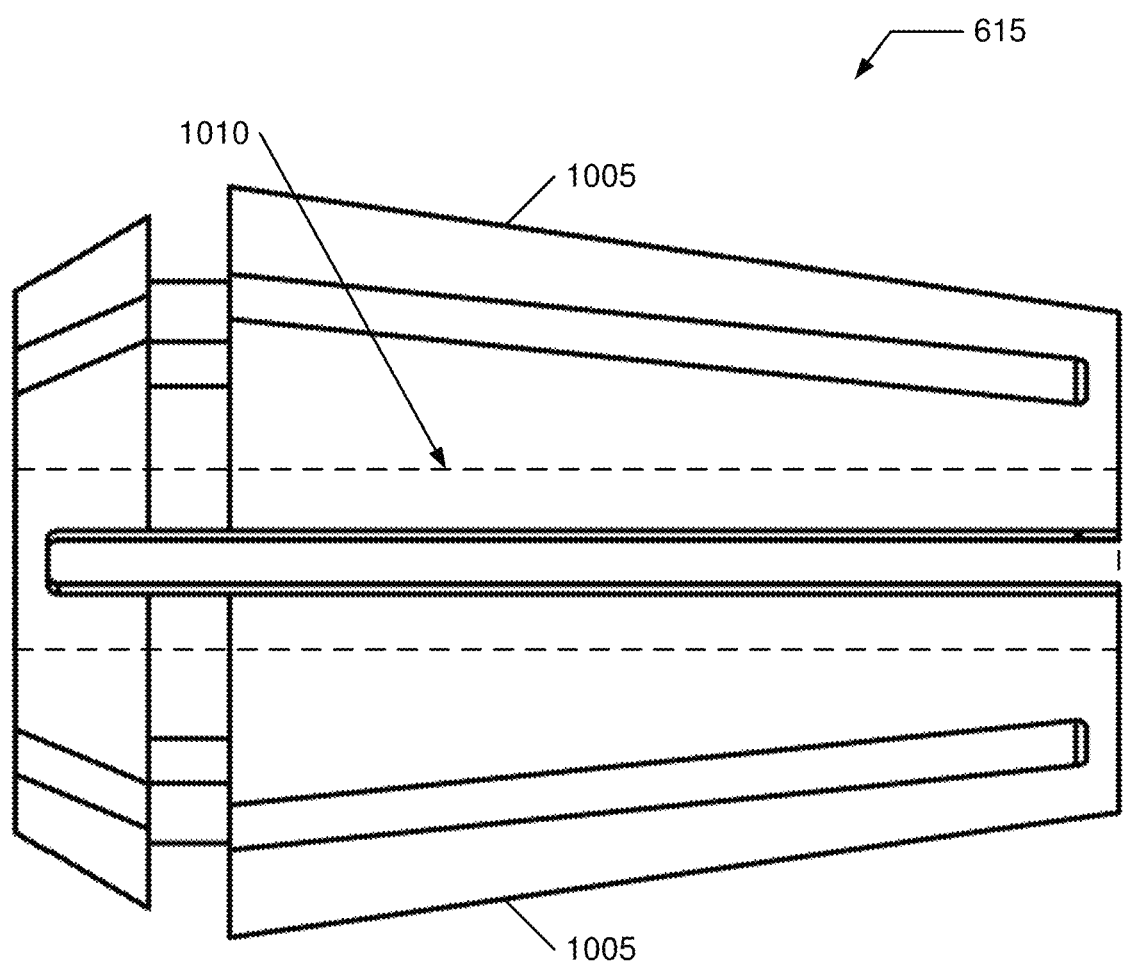
FIG. 12 illustrates a side sectional view of the collet of FIG. 10.

FIG. 10-FIG. 12 illustrate details of collet chuck 615. FIG. 10 illustrates a perspective view of collet chuck 615 of graft platform 500; FIG. 11 illustrates an end view of collet chuck 615 of FIG. 10; and FIG. 12 illustrates a side sectional view of collet chuck 615 of FIG. 10. Collet chuck 615 includes an N number, N≥2, of moveable tabs 1005 that collectively define a longitudinal tunnel 1010. N may be any integer two or greater and may often be an even number, for example N is an element of the set {2, 3, 4, 5, 6, 7, 8, 9, 10, 11, 12, . . . } depending upon various design considerations in compressing and shaping an outer perimeter of graft 300 to produce graft 400. In FIG. 10-FIG. 12, N=4. In FIG. 8 and FIG. 9, N=7.

In operation, platform 500 may include one or more different modalities for decreasing D1 of graft 300 and providing D2 of graft 400 that may be significantly smaller. One modality includes inserting all or portion of graft 300 into one or both collet chucks 615 (chucks 615 may have a length to accommodate the intended use. A single chuck 615 that is long enough may compress an entire length of graft 300. The tightening of the collet nut while some of all of graft 300 is disposed inside the longitudinal tunnel of the corresponding collet chuck will compress D1 of graft 300 to D2 of graft 400.

In other embodiments, a portion of each end, up to one-half, of graft 300 is installed into each of two opposing collet chucks on platform 500. That end portion in each collet chuck may then be compressed by tightening the corresponding collet nut. In this example, one-half of graft 300 is compressed by each stage. Variations are possible, such as where ⅓ of graft 300 is installed into one chuck and the remainder ⅔ of graft 300 installed into the other chuck. This allows for each end or portion of each end to be compressed to different diameters (the compressed diameter of one end may be different than the compressed diameter of the opposite end). Some procedures or protocols may be advantaged by producing differently sized tunnels in the different bones—one tunnel size in a femur and a different one in the tibia for example. Some embodiments of the present invention allow for this as necessary or desired.

Another possible modality for decreasing D1 of graft 300 is to use platform 500 to grip ends of graft 300 in each housing and then to use the drive rod to separate the housings. By using the torque wrench, an operator under stands how much tension is applied to graft 300 intermediate the gripped ends which tensions, stretches, and thins the intermediate portion. The degree of thinning of this intermediate portion is dependent upon the force applied and the tensile and compressive moduli (mechanical properties) of graft 300. As long as the thinning occurs in the elastic deformation range, there will be a tendency for the intermediate portion thinned this way to return towards a thicker instance. The graft may also exhibit elastic and/or inelastic behavior frequently described in solids, where a subset of viscoelastic materials have a unique equilibrium configuration and ultimately recover fully after removal of a transient load, such that after being squeezed, they return to their original shape, given enough time. The transient strain is recoverable after the load or deformation is removed. Time scale for recovery may be short, or it may be so long as to exceed the observer's patience.

In some embodiments, it is thus possible to produce a diameter profile over a length L2 of graft 400. Typically graft 400 includes a single diameter D1 over the entire length L1. However, embodiments of the present invention may tailor each end or portion thereof with a desired diameter (the same or different from the other end) and with a desired diameter for the intermediate portion that is the same or different from either or both ends. Some amount of each end, and the intermediate portion, may have its diameter be relatively independently controlled. Any end or intermediate portion may have a greater or lesser diameter than another part of graft 400. The intermediate portion may have the same, larger, or smaller diameter than one or both end portions. The same is true of each end relative to the other end and the intermediate portion.

In the above discussion, the grafts and tunnels, and structures complementary thereto have been described as generally elongate circular cross-sectional structures (e.g., cylindrical tunnels). This is because the current procedures provide for drilling tunnels in the implicated bones and the drilling produces generally circular cross-sectional tunnels. In general all ACL reconstructive techniques, whether performed arthroscopically or open, utilize the particular technique of initially proposing the tibial and femoral tunnels with a "guide wire", which is drilled in the desired position, and after confirmation, over-drilled with a cannulated drill bit to produce a perfect cylindrical tunnel.

In some instances, it may be possible to produce tunnels in the bones, possibly utilizing different techniques and completely different technologies, with the tunnels having other than circular (e.g., cylindrical) cross-sections. Perhaps healing and recovery may be better achieved with a generally elliptical cross-section tunnel such as a frustrum (e.g., of a pyramid or cone or other closed three-dimensional cavity volume), a rectilinear cross-section tunnel, or a tunnel that has a varying diameter over its length. In some cases, a bone preparation tool may include a LASER, a 3 dimensional (3D) bone sculpting tools, or robotic instruments to define a desired regular/irregular/symmetric/asymmetric tunnel that varies from a same-sized cylindrical bore (iv) typically produced in the femur and the tibia for current ACL reconstructive techniques.

An advantage of some embodiments of the present invention when installing a compressed graft 400 into any of these alternative types of tunnels (as well as the cylindrical bores from a drill) is that the graft 400 may selectively expand to fill any variable profile of the tunnel in the femur and tibia.

Figure 13:
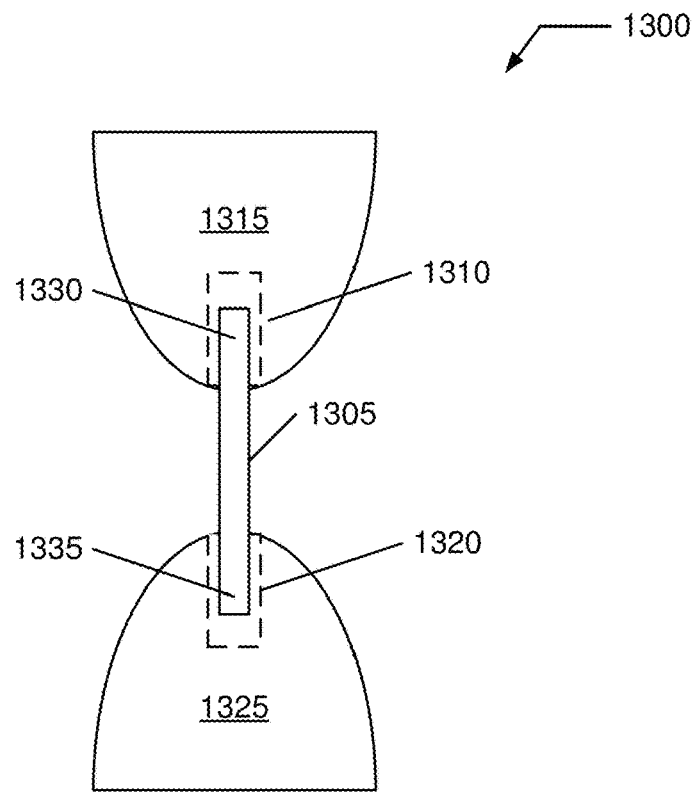
FIG. 13-FIG. 14 illustrates a reconstruction of an ACL in a pair of cylindrical bone tunnels.
Figure 14:
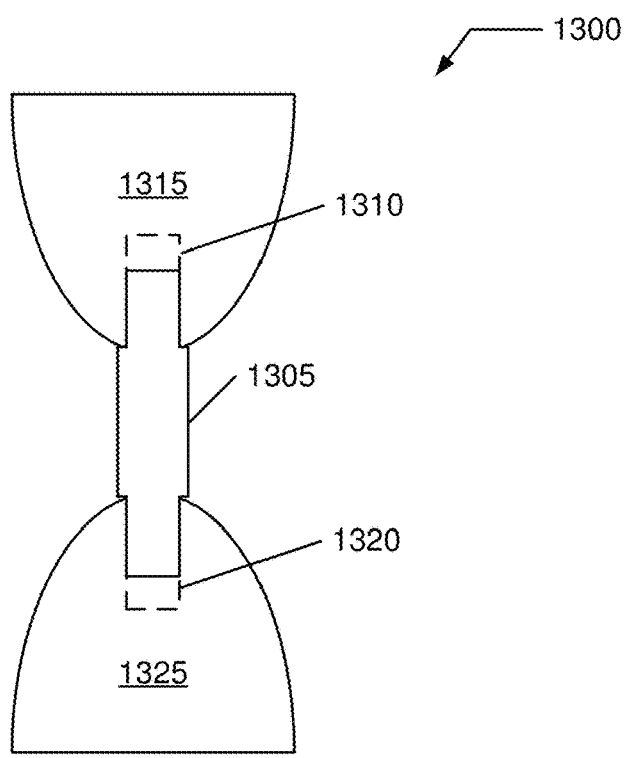

FIG. 13-FIG. 14 illustrates a reconstruction 1300 of an ACL in a pair of cylindrical bone tunnels. FIG. 13 illustrates pre-expansion of a compressed ACL graft 1305, such as an appropriately sized embodiment of graft 400 in FIG. 4 and FIG. 14 illustrates a post-installation-expansion of compressed ACL graft 1305. A bone tunnel 1310 is prepared in a portion of a femur 1315 and a bone tunnel 1320 is prepared in a portion of an adjacent tibia 1325. There may be several ways to prepare these bone tunnels, such as by installing a guide wire along a desired path and then using a cannulated drill bit to follow the guide wire to the desired depth. For example, these tunnels may have a diameter of about 9 millimeters and ACL graft may have an uncompressed diameter of about 10 millimeters and a compressed diameter of about 6-8 millimeters. With these dimensions, the compressed ACL graft may easily be installed into a prepared bone tunnel and an uncompressed ACL graft may produce significant lateral frictional forces holding it in place as the healing occurs and natural fixation completes itself to bond the uncompressed ACL graft into the prepared bone tunnels (with or without external fixation devices or structures).

After decompression of compressed ACL graft 1305 (in FIG. 14) the expanded ACL graft 1305 tightly fills each bone tunnel as it conforms to the cross-section profile (e.g. circle for a cylindrical bone tunnel). A diameter/profile of bone tunnel 1310 need not, but may be, the same as a diameter/profile of bone tunnel 1320. As long as portions of the diameters of the bone tunnels where the ACL graft is to be bonded (e.g., openings of the bone tunnels) are smaller than an original unexpanded diameter of the compressed ACL graft, temporary press-fit fixation from the decompression of the installed graft will secure the decompressing ACL graft into the bone tunnels and provide the advantages noted herein.

Once the bone tunnels are prepared, a first end 1330 of compressed ACL graft 1305 is installed into bone tunnel 1310 and a second end 1335 of compressed ACL graft 1305 is installed into bone tunnel 1320. As compressed graft decompresses it expands towards its original pre-compressed shape unless constrained (by a bone tunnel side wall for example).

Figure 15:
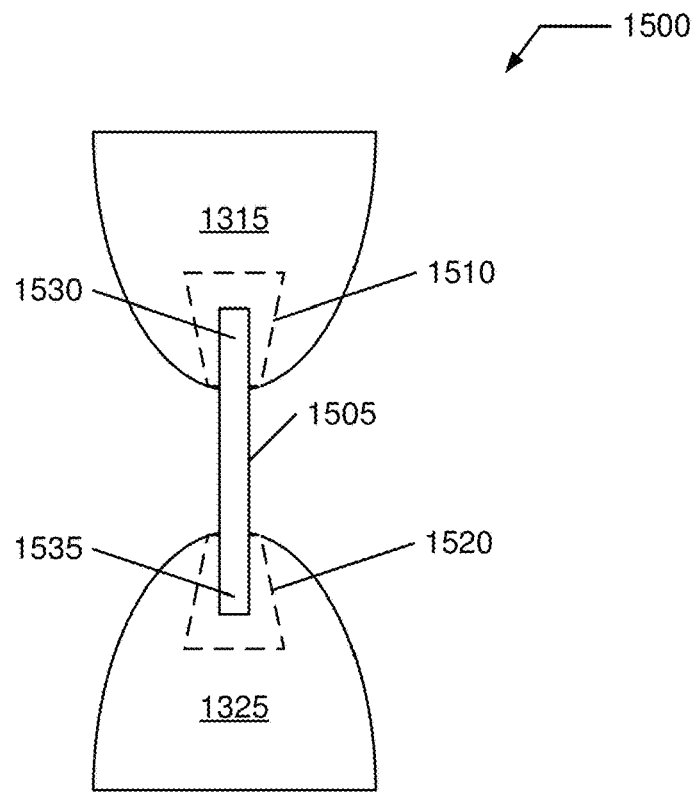
FIG. 15-FIG. 16 illustrates a reconstruction of an ACL into a pair of profiled bone tunnels.
Figure 16:
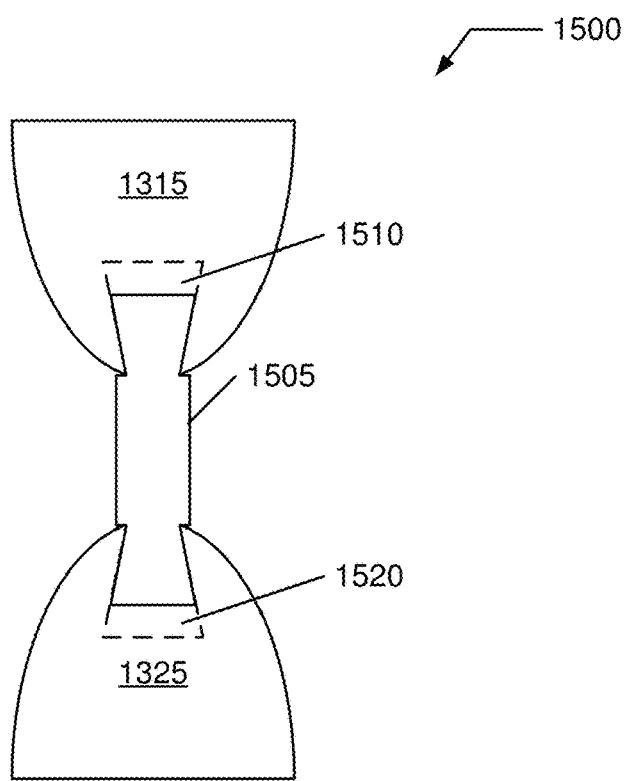

FIG. 15-FIG. 16 illustrates an alternative reconstruction 1500 of an ACL into a pair of profiled bone tunnels. FIG. 15 illustrates pre-expansion of a compressed ACL graft 1505 (which may be similar to ACL graft 1305 in FIG. 13), such as an appropriately sized embodiment of graft 400 in FIG. 4 and FIG. 14 illustrates a post-installation-expansion of compressed ACL graft 1505.

Alternative reconstruction 1500 is similar to reconstruction 1300 with the exception of the shape of the bone tunnels (and consequently the manner of the formation of the profiled bone tunnels in FIG. 15 and FIG. 16. The noted characteristic of the conforming decompression of a compressed ACL graft 1505 is used in this alternative to expand into specially profiled bone tunnels that may have a number of shapes where an opening profile is purposefully and significantly smaller than a cavity profile deeper into the bone.

A profiled bone tunnel 1510 is prepared in a portion of a femur 1315 and a profiled bone tunnel 1520 is prepared in a portion of an adjacent tibia 1325. There may be several ways to prepare these profiled bone tunnels, such as by use of a surgical robot or three-dimensional bone sculpting as described herein, for example in the discussion of FIG. 18 below. For example, these profiled tunnels may be generally shaped as a frustum have a narrower opening diameter of about 8 millimeters, a wider base diameter of about 9-10 millimeters, and the ACL graft may have an uncompressed diameter of about 10 millimeters and a compressed diameter of about 6-7 millimeters. With these dimensions, the compressed ACL graft may easily be installed into a prepared bone tunnel and a decompressing ACL graft, when decompressed, may produce significant frictional and mechanical forces (e.g., normal forces) holding it in place as the healing occurs and natural fixation completes itself to bond the uncompressed ACL graft into the prepared bone tunnels (with or without external fixation devices or structures).

After decompression of compressed ACL graft 1505 (in FIG. 15) the expanded ACL graft 1505 tightly fills each profiled bone tunnel as it conforms to the cross-section profile (e.g. circle for a cylindrical frustum bone tunnel). A shape of profiled bone tunnel 1510 need not, but may be, the same shape as the shape of profiled bone tunnel 1520. As long as portions of the diameters of the profiled bone tunnels where the ACL graft is to be bonded (e.g., openings of the bone tunnels) are smaller than an original unexpanded diameter of the compressed ACL graft, temporary "biologic press-fit" and mechanical fixation from the decompressing ACL graft will secure the ACL graft into the profiled bone tunnels and provide the advantages noted herein along with improved resistance to pull-out.

Once the bone tunnels are profiled, a first end 1530 of compressed ACL graft 1505 is installed into bone tunnel 1510 and a second end 1535 of compressed ACL graft 1505 is installed into bone tunnel 1520. As compressed graft decompresses it expands towards its original pre-compressed shape unless constrained (by a bone tunnel profiled side wall for example).

Figure 17:
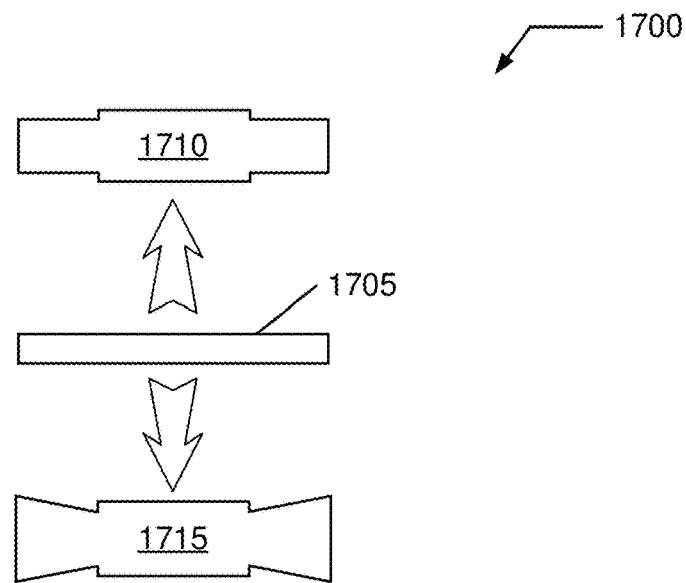
FIG. 17 illustrates different conforming expansions of a compressed ACL graft, dependent upon a preparation of a bone tunnel.

FIG. 17 illustrates different conforming expansions 1700 of a compressed ACL graft 1705, dependent upon a preparation of a bone tunnel and represent the examples from FIG. 13-FIG. 16. For example, when compressed ACL graft 1705 is installed into cylindrical bone tunnels (a simple example of a profiled bone tunnel), its decompression results in an uncompressed graft similar to graft 1710. When compressed ACL graft 1705 is installed into "inverted frustum" profiled bone tunnels (e.g., as illustrated in FIG. 15 and FIG. 16), its decompression results in an uncompressed graft similar to graft 1715. In general, the bone tunnel includes an opening in the prepared bone and a cavity defined in the prepared bone access through this opening. The opening defines a cross-section having an opening area. The cavity defines a cavity cross-section, parallel to the opening cross-section, that includes a cavity cross-section area. For cylindrical bone tunnels, the opening cross-section and the opening cross-section area matches the cavity cross-section and the cavity cross-section area. For asymmetrical bone tunnels, the opening cross-section and the cavity cross-section do not match, and the cavity cross-section area is greater than the opening cross-section area. The magnitude of this difference in area may vary on design considerations and procedure and may range from 5%-50% greater, to even more (e.g., greater than 100%). The area difference includes configurations to permit biological press fit fixation of the in-tunnel-expanded connective tissue, particularly without interference screws or cortical suspenders or other non-connective tissue structures installed or disposed within the bone tunnel.

Figure 18:
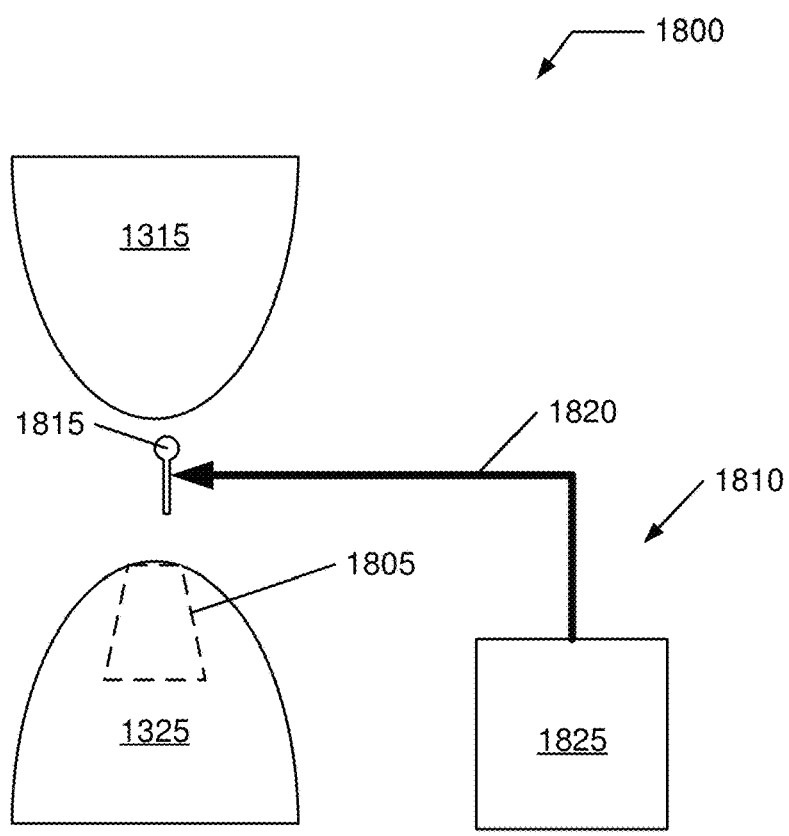
FIG. 18 illustrates a preparation of a profiled bone tunnel by an automated surgical apparatus.

FIG. 18 illustrates a bone profiling apparatus 1800 for a preparation of a profiled bone tunnel 1805 by an automated surgical apparatus 1810. In FIG. 18, apparatus 1810 has produced a first profiled bone tunnel 1805 in tibia 1325 and is preparing to produce a second profiled bone tunnel in femur 1315. Apparatus 1810 includes a bone preparation implement 1815 having a mechanical coupling 1820 (direct or indirect) between a controller 1825 (e.g., a stored program computing system including processor executing instructions from a memory including a user interface to set user options and parameters).

There are automated assistive surgical devices which may fill the role of apparatus 1810, such as robotic assisted surgical platforms (e.g., MAKO, da Vinci, Verb, Medtronic, TransEnterix, Titan Medical systems, NAVIO blue belt, and the like). These platforms provide positional control/limitation of surgical implements operated by a surgeon, such that the robotic tools (some of which utilize custom software and CT data) resist the movements by the surgeon that may attempt to deviate from a planned procedure, bone preparation, or other processing. These platforms are often installed into a known reference frame shared by the patient so precise position control/limitation may be imposed. Installing bone preparation tool 1815 (e.g., a high-speed rotating burr or the like) the surgeon may operate the platform to form a precisely profiled bone tunnel as described herein (e.g., first profiled tunnel 1805). A profiled tunnel may be initiated from a bit-prepared cylindrical tunnel and then profiled from there or apparatus 1810 may prepare the entirety of the profiled bone tunnel.

Further, current ACL techniques require that the surgeon estimate the length of the graft to fit the combined length of the tibial and femoral tunnels plus the intra-articular length of the ACL graft, housed in the notch. Despite best efforts mismatches between the length of the graft and the tunnels is not infrequent, which adversely affects the outcome. The use of automated surgical devices noted above has the advantage of providing the exact lengths of the tibial and femoral tunnels as well as the intra-articular length of the ACL graft within the notch. These techniques allow bone resection of any profile with varying trajectories and depths based on planned procedure, for example to within a millimeter. The tunnel lengths can be determined pre-operatively or intra-operatively and correlated with the length and diameter of the prepared allograft. Growth factors can be applied to pre-prepared allograft with external of and/or internal sheaths, or to auto-grafts prepared at the time of surgery.

Apparatus 1810 may be used to produce internal ridges, dimples, or other irregularities in the lateral wall of a bone tunnel (profiled or "conventional" cylindrical tunnel). The uncompressing ACL graft will fill these irregularities which may further promote fixation and healing.

Described above are embodiments (apparatus and methods) for production of a compressed connective tissue graft. Such a graft may be prepared from the patient or may be provided separately (e.g., a frozen pre-prepared allograft) that may be sized and compressed.

An embodiment of the present invention includes off-site advance preparation of compressed connective tissue graft that are shipped and stored in the compressed state. They may be frozen in the compressed state sufficiently partially thawed at the time of installation to allow appropriate decompression in situ. It may be that the pre-compressed allograft is delivered in a peel pack while freeze dried in the compressed state. The allograft is removed from the packaging and the surgeon will have some time for installation before it decompresses. In some cases, the allograft's decompression is accelerated by saline solution. Exposure of the compressed allograft to body fluids in the bone tunnels may also accelerate the decompression for fixation into the bone tunnel.

In other embodiments, a protective sheath may be provided that is installed after compression to maintain the connective tissue graft in the compressed state. Removal of the sheath allows for decompression. The sheath may be dissolvable in body fluids and installation into a bone tunnel begins the dissolution and decompression.

The sheath may be provided as a two-part element: an outer protective film prevents decompression and an inner layer that may temporarily inhibit decompression during the installation process. When ready to install, the outer layer is removed and the connective tissue graft (with inner layer) is inserted into the bone tunnel. Alternatively, the outer and inner sheaths of compressed ACL prepared grafts can be embedded with a combination of biological growth factors including the TGF family, bone morphogenic proteins (BMP), insulin like growth factors, matrix metalloproteinases, fibroblast growth factors, vascular endothelial growth factors, platelet derived growth factors, and or other stem cell derived growth factors (including epithelial and mesenchymal stromal cells), which alone or in combination can significantly improve healing of tendon to bone, promoting angiogenesis and osteogenesis at the tendon-bone interface after ACL reconstruction. The sheaths may also include other allogenic sources of growth factors such as amniotic membrane products and the like.

Figure 19:
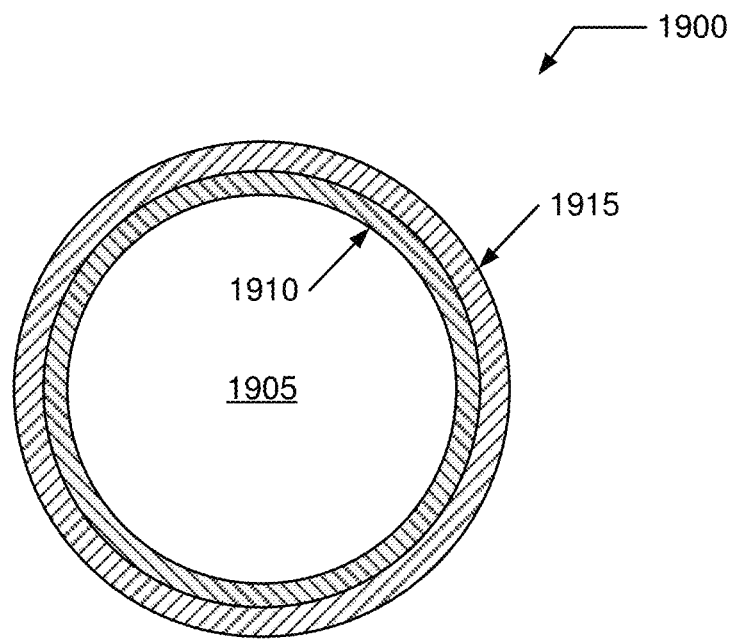
FIG. 19 illustrates an allograft system including a pre-compressed allograft with a sheathing subsystem having an outer sheath and an inner sheath.

FIG. 19 illustrates an allograft system 1900 including a pre-compressed allograft 1905 with a sheathing subsystem having one or more sheaths (e.g., an inner sheath 1910 and an outer sheath 1915). The sheathing subsystem may accomplish one or more functions depending upon implementation, to achieve desired goals as described herein. Those goals may include a number of functions, such as maintaining a pre-compressed allograft 1905 in its compressed mode until installed into a prepared bone tunnel for decompression as described herein. Other functions include enhancing preservation of sterility and delivery of growth factors into the bone tunnel at the graft/tunnel interface.

Figure 20:
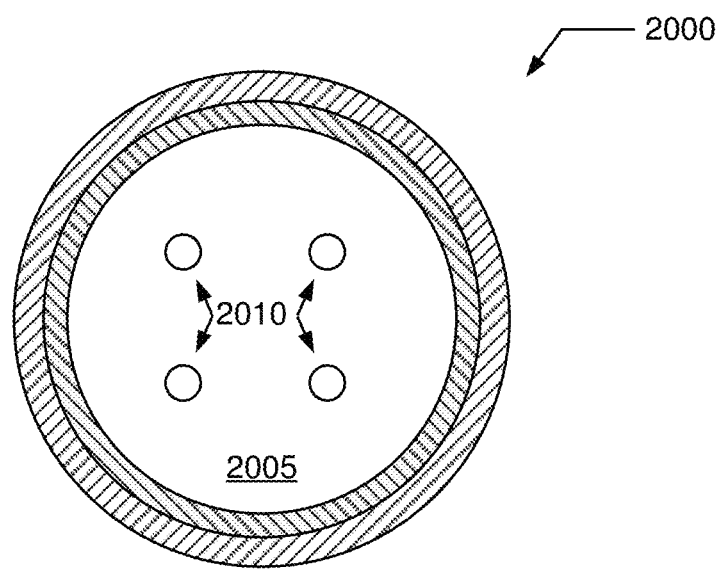
FIG. 20 illustrates an allograft system including a pre-compressed allograft with a prosthesis subsystem having at least one connective tissue prosthetic element.

FIG. 20 illustrates an allograft system 2000 including a pre-compressed allograft 2005 with an embedded prosthesis subsystem having at least one connective tissue prosthetic element 2010 that runs a length. There is a history of development and investigation of synthetic ACL grafts but have generally not proven to be successful. There are a number of problems of a pure synthetic connective tissue graft, including a) breakdown of the synthetic material with exposure in the joint that too often leads to synovitis and arthritis due to existence of the foreign material in joints; and b) not finding a synthetic graft that has equivalent material properties of connective tissue. There is not complete agreement on the mechanical properties needed or desired for such a synthetic graft: some materials discuss a "stiffness" of the synthetic material. However, it may be the case that a graft that has the similar "toughness properties" of native ACL may be preferable: i.e., more ductile than brittle (i.e. a larger plastic range).

Allograft system 2000 is believed to address some of these drawbacks as it is a hybrid system: native connective tissue on the outside with an embedded prosthetic element(s) inside. Illustrated is embedding the prosthetic elements inside a pre-compressed allograft as described herein. Some embodiments may embed these synthetic elements within a conventional allograft and use an alternative fixation method.

The one or more prosthetic elements may each include single strands of suitable material (e.g., natural and/or synthetic material) or may include a weave of such materials (including composite weaves of multiple different materials). The one or more embedded prosthetic elements do not provide for intra-articular bone exposure.

When embedded into a pre-compressed, the expansion fixation of the decompressing allograft into a bone tunnel secures the prosthetic elements along with the outer native decompressed graft.

Figure 21:
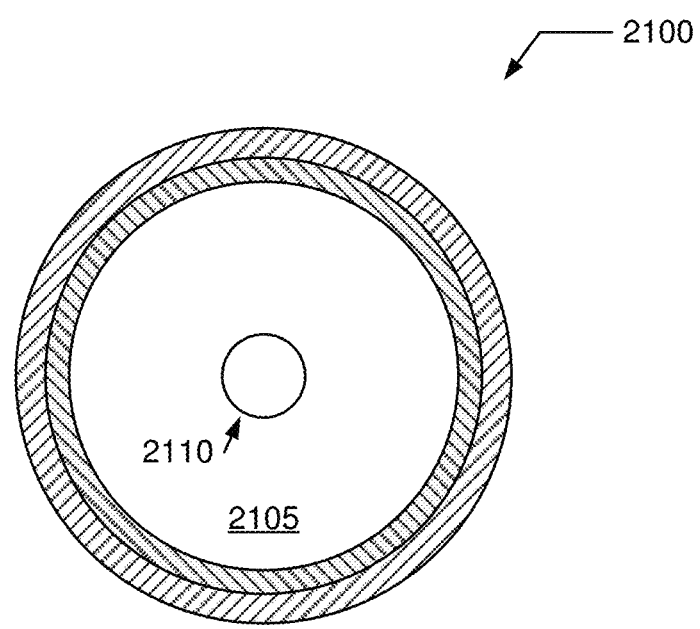
FIG. 21 illustrates an allograft system including a pre-compressed allograft with an expansion subsystem having at least one expansion element.

FIG. 21 illustrates an allograft system 2100 including a pre-compressed allograft 2105 with an expansion subsystem having at least one expansion element 2110 disposed in one or more portions that are to be expanded. These portions may be one or both end portions and/or middle portion. In some cases, the at least one expansion element may run a length of the compressed allograft. In many embodiments, the enlargement of a pre-compressed allograft has been described as a generally passive process in which a compressed allograft is allowed to decompress. It is the case that under some circumstances that natural connective tissue may expand somewhat when subjected to bodily fluids or pre-operative fluid baths (e.g., saline solution) for thawing an often-frozen allograft.

Allograft system 2100 includes an active expansion system which expands compressed native connective tissue. Expansion may be accomplished by use of the at least one embedded expansion element 2110. This at least one expansion element 2110 may be embedded into a pre-compressed allograft as described herein or embedded into a conventional allograft. In some implementations, the at least one expansion element 2110 may be part of, included within, integrated with, or provided as part of at least synthetic prosthetic element as illustrated in FIG. 21. For example, a structure may have a dual use of providing the synthetic prosthetic element and the expansion element.

System 2100 introduces the concept of "internal expandable structures (e.g., tubes) for configuring/implementing biological press fit interference fixation of pre-compressed ACL grafts (it being noted that herein that these expandable structures may be used with conventional allografts and/or with conventional fixation methods).

One method to increase tendon/bone interface pressures (in lieu of interference screws or cortical suspending hardware) is a new concept of introducing expandable tubes, cages or stents within the ends of the allografts, and allowing the tube, cage or stent to expand passively or actively, to subsequently increase graft bone interface pressures to assure "direct" type fixation.

The material for the "intra graft tubes" can be synthetic non-absorbable material such as plastic and or polyester or similar material; or absorbable material. Current methods of "in tunnel" fixation compromise "tendon/bone surface contact area". An embodiment of the present invention may include a method, apparatus, and system where the graft, or synthetic material disposed within the graft, may be expanded which is juxtaposed and pressed, in some instances uniformly pressed, to interior surface walls of the prepared bone tunnel. In this manner tendon/bone interface is not required to be compromised by the addition of hardware fixation solutions. A surgeon may desire to supplement this "pure" non-hardware biologic press fit fixation with hardware, such as interference screws and/or cortical suspensors. The hardware may be more limited and less intrusive as it is not required to be the primary fixation.

Absorbable material could be polymer based as in polylactide (PLLA), polyglycolic acid (PGA), copolymers (PGA/PLA) poly paradiaxanone, and various stereoisomers of lactic acid, along with various bio-composite materials including a mix of polymers noted above plus calcium phosphate etc. Alternatively, absorbable material could be magnesium alloy based with similar functionality where the material absorbs over time (i.e. over three months).

The expansion of the tubes may occur passively over defined period of time or actively. Active expansion can be done by balloon expansion after implantation of the graft, similar to what is done with balloon expandable stents in vascular procedures, where inflation of a balloon within the tube expands the tube inside the graft to increase intra graft pressure on the graft/bone interface, without any contact of the tube (whether bio absorbable or synthetic) with the tendon/bone interface. This concept theoretically eliminates the current problem of screw breakdown and release of inflammatory cytokines associated with tunnel widening and poor graft healing. Active expansion can also occur by "unsheathing the tube" or "pulling a rip cord" immediately after implantation of the graft, which is also done in vascular procedures.

The system and methods above have been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A method for an installation of a connective-tissue-structure within a prepared bone tunnel in a portion of bone, the connective-tissue structure defining, prior to the installation, a non-compressed connective tissue structure having a non-compressed perimeter including a non-compressed cross-sectional area, the bone tunnel configured to receive an installation of a precompressed connective-tissue-structure produced from the non-compressed connective tissue structure through a bone tunnel opening, the bone tunnel including a bone tunnel portion and the bone tunnel opening having a tunnel perimeter defining a bone tunnel opening cross-sectional area less than the non-compressed cross-sectional area, the precompressed connective-tissue-structure including a precompressed exterior perimeter defining a precompressed cross-sectional area less than the bone tunnel opening cross-sectional area and an end, and the installation including the end disposed within the bone tunnel portion, wherein the precompressed connective-tissue-structure includes an expansion bias configured to increase the exterior perimeter after disposition within the bone tunnel portion, comprising the steps of:

operating a bone-shaping implement configured to produce a non-cylindrical bone tunnel having a bone tunnel profile including the bone tunnel portion; and shaping the portion of bone of the bone tunnel portion using said bone-shaping implement to create a non-cylindrical bone tunnel portion;

installing the precompressed connective tissue within said non-cylindrical bone tunnel portion producing an installed precompressed connective-tissue-structure;

and thereafter decompressing automatically said installed precompressed connective-tissue-structure within said non-cylindrical bone tunnel portion producing a decompressed connective-tissue-structure, said decompressed connective-tissue-structure engaging the non-cylindrical bone tunnel portion;

wherein said decompressed connective-tissue-structure includes both the end and a decompressed exterior connective tissue perimeter defining a decompressed cross sectional area greater than the precompressed cross-sectional area and equal to or greater than the bone tunnel opening cross-sectional area; and wherein said non-cylindrical bone tunnel portion is configured, in cooperation with said decompressed connective-tissue-structure installed within the bone tunnel, for a non-sliding rententive fixation of said decompressed connective-tissue-structure within said non-cylindrical bone tunnel by direct application of a press fit fixation force at a bone-decompressed-connective-tissue-structure interface inside the prepared bone tunnel;

wherein said non-sliding rententive fixation does not include a foreign fixation body disposed within the bone tunnel portion.

2. A method for an installation of a connective-tissue-structure within a prepared bone tunnel in a portion of bone, the connective-tissue structure defining, prior to the installation, a non-compressed connective tissue structure having a non-compressed perimeter including a non-compressed cross-sectional area, the bone tunnel configured to receive an installation of a precompressed connective-tissue-structure produced from the non-compressed connective tissue structure through a bone tunnel opening, the bone tunnel including a bone tunnel portion and the bone tunnel opening having a tunnel perimeter defining a bone tunnel opening cross-sectional area less than the non-compressed cross-sectional area, the precompressed connective-tissue-structure including a precompressed exterior perimeter defining a precompressed cross-sectional area less than the bone tunnel opening cross-sectional area and an end, and the installation including the end disposed within the bone tunnel portion, wherein the precompressed connective-tissue-structure includes an expansion bias configured to increase the exterior perimeter after disposition within the bone tunnel portion, comprising the steps of:

operating a bone-shaping implement configured to produce a non-cylindrical bone tunnel having a bone tunnel profile including the bone tunnel portion; and shaping the portion of bone of the bone tunnel portion using said bone-shaping implement to create a non-cylindrical bone tunnel portion;

installing the precompressed connective tissue within said non-cylindrical bone tunnel portion producing an installed precompressed connective-tissue-structure;

and thereafter decompressing automatically said installed precompressed connective-tissue-structure within said non-cylindrical bone tunnel portion producing a decompressed connective-tissue-structure, said decompressed connective-tissue-structure engaging the non-cylindrical bone tunnel portion;

wherein said decompressed connective-tissue-structure includes both the end and a decompressed exterior connective tissue perimeter defining a decompressed cross sectional area greater than the precompressed cross-sectional area and equal to or greater than the bone tunnel opening cross-sectional area; and wherein said non-cylindrical bone tunnel portion is configured, in cooperation with said decompressed connective-tissue-structure installed within the bone tunnel, for a non-sliding rententive fixation of said decompressed connective-tissue-structure within said non-cylindrical bone tunnel by direct application of a press fit fixation force at a bone-decompressed-connective-tissue-structure interface inside the prepared bone tunnel;

wherein said steps do not include a use of a pre-determined guide wire and an over drilling technique.

3. A method for an installation of a connective-tissue-structure within a prepared bone tunnel in a portion of bone, the connective-tissue structure defining, prior to the installation, a non-compressed connective tissue structure having a non-compressed perimeter including a non-compressed cross-sectional area, the bone tunnel configured to receive an installation of a precompressed connective-tissue-structure produced from the non-compressed connective tissue structure through a bone tunnel opening, the bone tunnel including a bone tunnel portion and the bone tunnel opening having a tunnel perimeter defining a bone tunnel opening cross-sectional area less than the non-compressed cross-sectional area, the precompressed connective-tissue-structure including a precompressed exterior perimeter defining a precompressed cross-sectional area less than the bone tunnel opening cross-sectional area and an end, and the installation including the end disposed within the bone tunnel portion, wherein the precompressed connective-tissue-structure includes an expansion bias configured to increase the exterior perimeter after disposition within the bone tunnel portion, comprising the steps of:

operating a bone-shaping implement configured to produce a non-cylindrical bone tunnel having a bone tunnel profile including the bone tunnel portion; and shaping the portion of bone of the bone tunnel portion using said bone-shaping implement to create a non-cylindrical bone tunnel portion;

installing the precompressed connective tissue within said non-cylindrical bone tunnel portion producing an installed precompressed connective-tissue-structure; and thereafter decompressing automatically said installed precompressed connective-tissue-structure within said non-cylindrical bone tunnel portion producing a decompressed connective-tissue-structure, said decompressed connective-tissue-structure engaging the non-cylindrical bone tunnel portion;

wherein said decompressed connective-tissue-structure includes both the end and a decompressed exterior connective tissue perimeter defining a decompressed cross sectional area greater than the precompressed cross-sectional area and equal to or greater than the bone tunnel opening cross-sectional area; and wherein said non-cylindrical bone tunnel portion is configured, in cooperation with said decompressed connective-tissue-structure installed within the bone tunnel, for a non-sliding rententive fixation of said decompressed connective-tissue-structure within said non-cylindrical bone tunnel by direct application of a press fit fixation force at a bone-decompressed-connective-tissue-structure interface inside the prepared bone tunnel;

wherein said steps include inserting the precompressed connective-tissue-structure into the prepared bone tunnel portion and anchoring the precompressed connective-tissue-structure within the non-cylindrical bone tunnel portion without a foreign body.

* * * * *